(12) United States Patent
Dodey et al.

(10) Patent No.: US 6,211,181 B1
(45) Date of Patent: Apr. 3, 2001

(54) 1-BENZENESULFONYL PYRROLIDINE DERIVATIVES AS BRADYKININ RECEPTOR ANTAGONISTS

(75) Inventors: Pierre Dodey; Michel Bondoux, both of Fontaine-les-Dijon; Patrick Houziaux, Bazemont; Martine Barth, Montfort-1'Amaury; Khan Ou, Hauteville-les-Dijon, all of (FR)

(73) Assignee: Fournier Industrie et Sante, Paris (FR)

( * ) Notice: Subject to any disclaimer, the term of this patent is extended or adjusted under 35 U.S.C. 154(b) by 0 days.

(21) Appl. No.: 09/091,988

(22) PCT Filed: Dec. 23, 1996

(86) PCT No.: PCT/FR96/02066

§ 371 Date: Oct. 27, 1999

§ 102(e) Date: Oct. 27, 1999

(87) PCT Pub. No.: WO97/24349

PCT Pub. Date: Jul. 10, 1997

(30) Foreign Application Priority Data

Dec. 29, 1995 (FR) .................................. 95-15706

(51) Int. Cl.$^7$ .................. A61K 31/4709; A61K 31/496; C07D 215/12; C07D 401/02; C07D 401/14

(52) U.S. Cl. .................... 514/253.06; 514/314; 544/363; 546/166

(58) Field of Search ............... 544/363; 546/166; 514/253.06, 314

(56) References Cited

U.S. PATENT DOCUMENTS 5,288,725  2/1994  Witherup et al. .

FOREIGN PATENT DOCUMENTS 0 261 539  3/1988  (EP) .
0 596 406  5/1994  (EP) .
0 622 361  11/1994  (EP) .

*Primary Examiner*—Joseph K. McKane
*Assistant Examiner*—Taofiq A. Solola
(74) *Attorney, Agent, or Firm*—Evenson, McKeown, Edwards & Lenahan, P.L.L.C.

(57) ABSTRACT

This invention relates to compounds of the formula

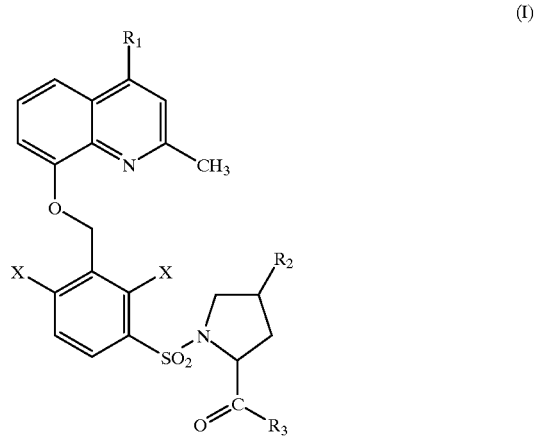

(I)

where X is halogen, $R_1$ is H or a $C_1$–$C_3$ alkyl, $R_2$ is H or OH and $R_3$ is one of

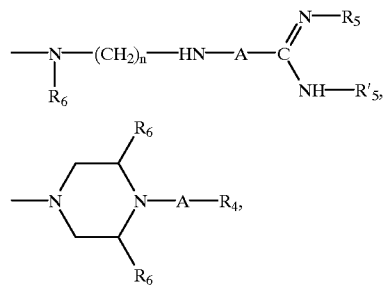

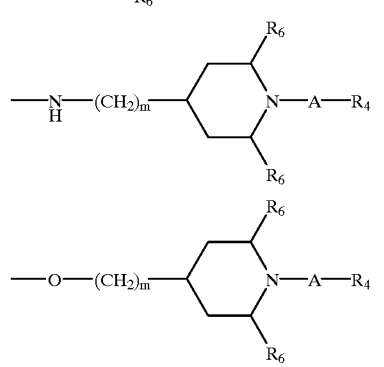

in which A is a single bond or a —CO(CH$_2$)$_p$—NH— group, $R_4$ is H or —C(=NR$_5$)NHR'$_5$, $R_5$ and R'$_5$ are each H or a $C_1$–$C_6$ alkyl group, $R_6$ is H or a $C_1$–$C_3$ alkyl group, m is 0, 1 or 2; n is 2, 3 or 4; p is 1, 2 or 3; plus their acid addition salts. The invention likewise relates to the method for their preparation and their therapeutic applications.

7 Claims, No Drawings

1-BENZENESULFONYL PYRROLIDINE DERIVATIVES AS BRADYKININ RECEPTOR ANTAGONISTS

This is a 371 of PCT/FR96/02066 filed Dec. 23, 1996.

FIELD OF THE INVENTION

The present invention relates to novel compounds belonging to the benzenesulfonamide family and more particularly to 1-benzenesulfonylpyrrolidine compounds, to the process for their preparation and to their use in therapeutics.

In particular, these novel compounds have an antagonistic action on the bradykinin $B_2$ receptor and are useful in therapeutics, especially for the treatment of pain, inflammation, asthma and allergic rhinitis.

PRIOR ART

It is known that one of the possible treatments for certain pathological conditions of a painful and/or inflammatory nature (such as asthma, rhinitis, septic shock, toothache, etc.) is to inhibit the action of certain hormones such as bradykinin or kallidin. These peptide hormones are in fact involved in a large number of physiological processes, some of which are closely associated with these pathological conditions.

Although no product possessing this mode of action has yet been marketed, numerous studies have been undertaken in order to create compounds capable of antagonizing the bradykinin receptors. Bradykinin is a peptide hormone consisting of 9 amino acids (Arg—Pro—Pro—Gly—Phe—Ser—Pro—Phe—Arg) and kallidin is a peptide hormone (Lys—Arg—Pro—Pro—Gly—Phe—Ser—Pro—Phe—Arg) which contains an additional amino acid (Lys) compared with bradykinin. It is known that earlier studies made it possible to obtain peptides which interact with the bradykinin receptors: some of them, like bradycor (CP.0127 from Cortech), icatibant (HOE 140 from Hoechst) ["bradycor" and "icatibant" are international non-proprietary names (INN)] or NPC 17761 (from Scios-Nova), have an inhibitory action on the binding of bradykinin to the bradykinin $B_2$ receptor. More recently, non-peptide compounds have been proposed as antagonists towards the binding of bradykinin to its $B_2$ receptor, especially in published patent applications EP-A-0596406 and EP-A-0622361. It is also known that certain compounds which are structurally related to the compounds referred to in the two patent applications cited above have already been described for their possible anti-thrombotic properties, especially in DE-A-3617183 and EP-A-0261539.

OBJECT OF THE INVENTION

There is a need for reducing or eliminating pain and inflammation in mammals and particularly in man.

To meet this need, a novel technical solution has been sought which is effective on the one hand in the treatment of pain, irrespective of its origin, especially pain associated with inflammatory phenomena, and on the other hand in the treatment of inflammation.

According to the invention, it is proposed to provide a novel technical solution which involves competitive binding, at the bradykinin $B_2$ receptor, between (i) bradykinin and related or analogous hormones such as kallidin, and (ii) an antagonist, and utilizes benzenesulfonamide compounds which are structurally different from the known products mentioned above and which limit or substantially inhibit the binding of bradykinin and said analogous hormones to said bradykinin $B_2$ receptor.

In accordance with this novel technical solution, it is proposed according to a first aspect of the invention to provide benzenesulfonamide compounds as novel industrial products, according to a second aspect of the invention to provide a process for the preparation of these compounds, and according to a third aspect of the invention to provide the use of these compounds, especially in therapeutics, as analgesic and/or anti-inflammatory active ingredients.

SUBJECT OF THE INVENTION

In accordance with the novel technical solution of the invention, a benzenesulfonylpyrrolidine compound is recommended as a novel industrial product, said compound being characterized in that it is selected from the group consisting of:

(i) the compounds of the formula

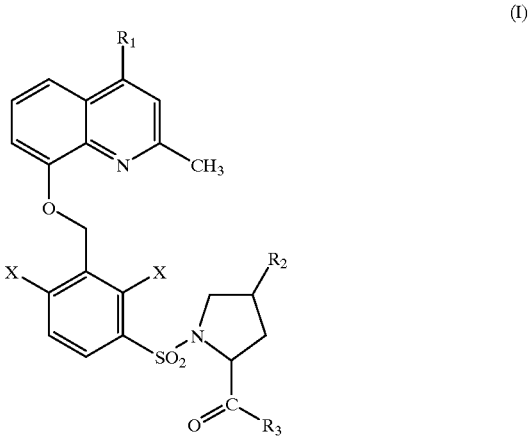

(I)

in which:

X is a halogen atom, $R_1$ is a hydrogen atom or a linear or branched $C_1$–$C_3$ alkyl group, $R_2$ is a hydrogen atom or an OH group, $R_3$ is a group

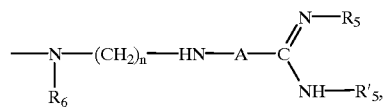

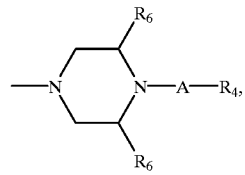

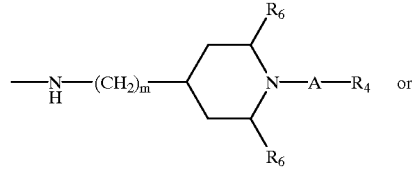

-continued

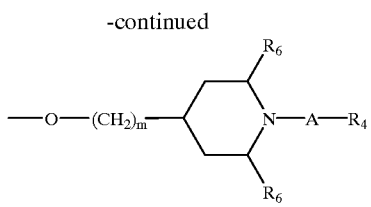

A is a single bond or a group —CO—(CH$_2$)$_p$—NH—,
R$_4$ is a hydrogen atom or a group

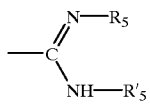

R$_5$ and R'$_5$, which are identical or different, are each a hydrogen atom or a linear, branched or cyclized C$_1$–C$_6$ alkyl group,
R$_6$ is a hydrogen atom or a linear or branched C$_1$–C$_3$ alkyl group,
m is a number with a value of 0, 1 or 2,
n is a number with a value of 2, 3 or 4, and
p is a number with a value of 1, 2 or 3; and
(ii) their addition salts.

According to the invention, a process for the preparation of the compounds of formula I and their addition salts is also recommended.

The use of a substance selected from the compounds of formula I and their non-toxic addition salts is also recommended for obtaining a drug intended for use in therapeutics to combat pathological conditions involving bradykinin or its analogs, in particular to combat pain, and especially in the treatment or prevention of pathological conditions associated with inflammatory or painful states.

DETAILED DESCRIPTION OF THE INVENTION

In general formula I of the compounds of the invention, halogen atom is understood as meaning a fluorine, chlorine, bromine or iodine atom, the preferred halogen being the chlorine atom.

C$_1$–C$_3$ alkyl group with a linear or branched hydrocarbon chain is understood here as meaning the methyl, ethyl, propyl and 1-methylethyl groups. Linear, branched or cyclized C$_1$–C$_6$ alkyl groups are understood as meaning especially the methyl, ethyl, propyl, butyl, pentyl, hexyl, 1-methylethyl, 1-methylpropyl, cyclopentyl and cyclohexyl groups.

In the compound of formula I, the nitrogen heterocycle of the pyrrolidine type carrying the groups COR$_3$ and R$_2$ can comprise 1 or 2 asymmetric carbon atoms. According to the invention, these carbon atoms can have the (R,S), R or S configuration; the carbon carrying the group COR$_3$ will preferably have the S configuration.

"Addition salts" are understood here as meaning the acid addition salts obtained by reacting a compound of formula I with a mineral or organic acid. The preferred mineral acids for salifying a basic compound of formula I are hydrochloric, hydrobromic, phosphoric and sulfuric acids. The preferred organic acids for salifying a basic compound of formula I are methanesulfonic, maleic, fumaric, oxalic, citric and trifluoroacetic acids.

Room temperature (RT) is understood here as meaning a temperature of between 15 and 25° C., and temperature close to RT is understood here as meaning a temperature of between 5 and 35° C.

The process recommended according to the invention for the preparation of the compounds of formula I and their addition salts comprises the steps which consist in:
1) reacting a compound of the formula (II)

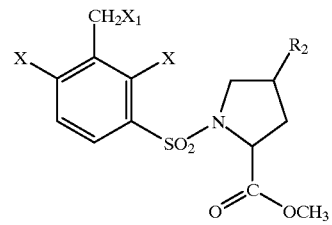

in which X and X$_1$ are each a halogen,
R$_2$ is a hydrogen atom or an OH group, and
the carbon carrying the group COOCH$_3$ and the carbon carrying the group R$_2$, when the latter is not the hydrogen atom, independently of one another have the (R,S), (R) or (S) configuration,
with a compound of the formula (III)

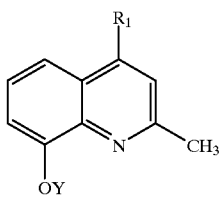

in which:
R$_1$ is a hydrogen atom or a C$_1$–C$_3$ alkyl group, and
Y is an alkali metal such as sodium or potassium,
in an anhydrous solvent, for example dimethylformamide, at a temperature of between 0 and 50° C., for 0.5 to 5 hours, to give a compound of the formula (IV)

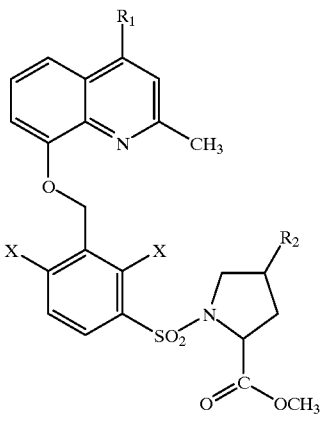

in which X, R$_1$ and R$_2$ are as defined in the starting compounds and the carbon atoms carrying the substituents COOCH$_3$ and R$_2$ retain the same configuration as in the compound II above;
2) subjecting the resulting compound IV to alkaline hydrolysis of the ester linkage by reaction with an aqueous solution of a metal hydroxide (especially NaOH) in an inert solvent, especially dimethoxyethane, at a temperature of between 10 and 50° C., for 1 to 30 hours, to give, after acidification, the acid compound of the formula

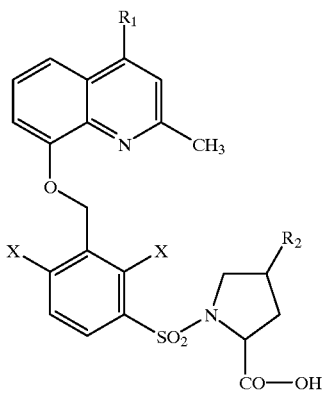

(V)

in which X, $R_1$ and $R_2$ are as defined in the compound IV above;

3) reacting the resulting acid V with an alcohol or an amine of the formula

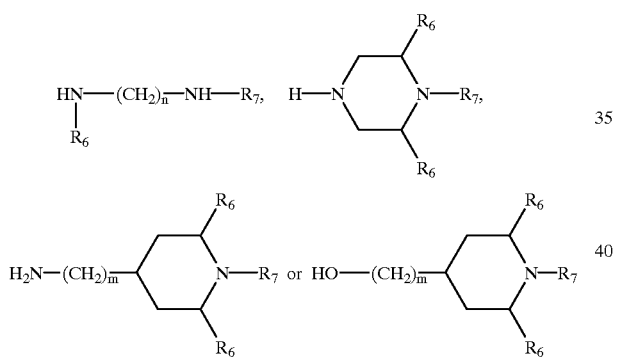

in which:

m is 0, 1 or 2, n is 2, 3 or 4, $R_6$ is a hydrogen atom or a $C_1$–$C_3$ alkyl group, and $R_7$ is an amino-protecting group, for example a Boc [(1,1-dimethylethoxy)carbonyl] group or, in certain cases, a hydrogen atom, in a solvent, for example dichloromethane, in the presence of one or more activators, for example 1-hydroxy-7-azabenzotriazole (HOAT) and 1-[3-(dimethylaminopropyl)-3-ethyl]carbodiimide (EDCI) hydrochloride, at a temperature close to room temperature, for 2 to 50 hours, to give a compound of the formula

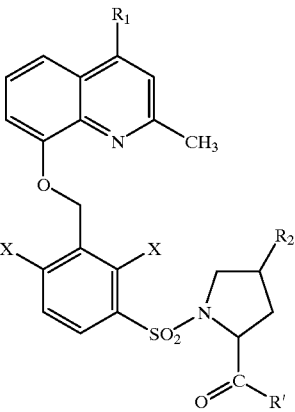

(VI)

in which:

X, $R_1$ and $R_2$ are as defined above and R' is one of the following groups:

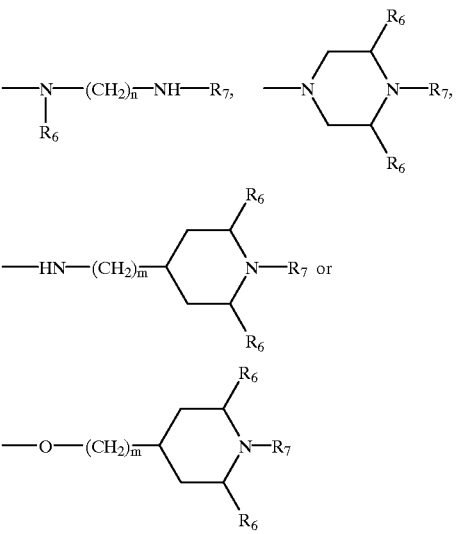

in which m, n, $R_6$ and $R_7$ are as defined above;

4) if necessary, i.e. when $R_7$ is an amino-protecting group, deprotecting the compound of formula VI thus obtained in the previous step by reacting said compound of formula VI with an acid, for example trifluoroacetic acid or hydrochloric acid, optionally in the presence of a free radical scavenger, for example anisole, and optionally in a solvent, for example ethyl acetate, at a temperature close to room temperature, for 1 to 20 hours, to give the compound of general formula VI described above in which $R_7$ is a hydrogen atom (corresponding to the compound of formula I in which A is a single bond and $R_4$ is a hydrogen atom);

5) if necessary, reacting the resulting compound of formula VI in which $R_7$ is a hydrogen atom with a compound of the formula

$R_8$—NH—$(CH_2)_p$—COOH in which p is a number equal to 1, 2 or 3, and $R_8$ is an amino-protecting group of the oxycarbonyl type, especially an alkoxycarbonyl group such as Boc [(1,1-dimethylethoxy)carbonyl], under reaction conditions analogous to those described in step 3 above, to give a compound of the formula

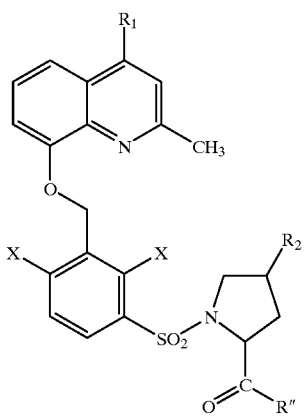

(VII)

in which X, $R_1$ and $R_2$ are as defined above and R" is a group

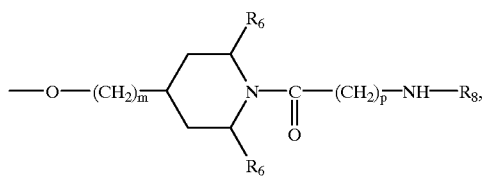

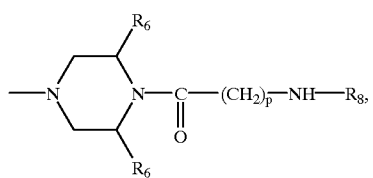

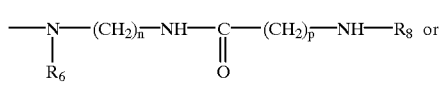

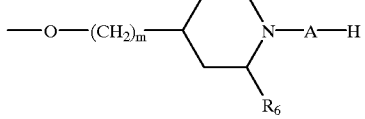

in which m, n, p, $R_6$ and $R_8$ are as defined above;

6) reacting the compound of formula VII obtained above according to step 5, under conditions analogous to those described in step 4 above, so as to replace the amino-protecting group $R_8$ with a hydrogen atom to give a compound of the formula

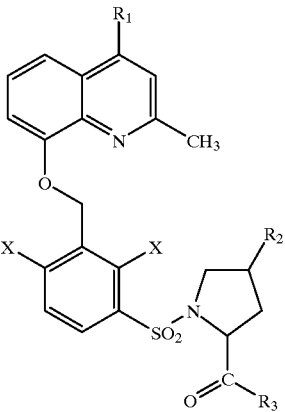

(I)

in which X, $R_1$ and $R_2$ are as defined above and R is a group

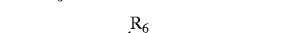

in which m, n and $R_6$ are as defined above and A is the group $-CO-(CH_2)_p-NH-$, in which p is a number equal to 1, 2 or 3;

7) if necessary, reacting a compound of formula I obtained in one of steps 4 or 6 above, in which A is a single bond or a group

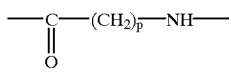

with a compound of the formula

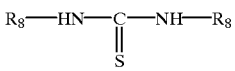

in which $R_8$ is an amino-protecting group of the oxycarbonyl type, especially an alkoxycarbonyl group such as Boc [(1,1-dimethylethoxy)carbonyl], in a solvent, for example dimethylformamide, in the presence of a base, for example triethylamine, and in the presence of mercuric chloride, at a temperature of between 0 and 30° C., for 1 to 6 hours, to give the compound of the formula (VII)

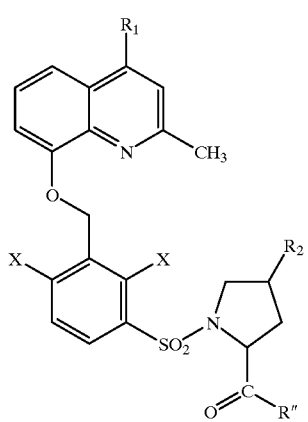

in which $R_1$, $R_2$ and X are as defined above and R" is a group

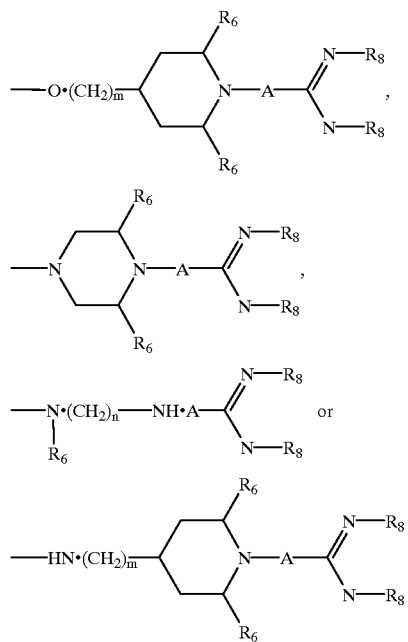

in which:
A is a single bond or the group —CO—$(CH_2)_p$—NH—, and
n, m, p, $R_6$ and $R_8$ are as defined above; and
8) deprotecting the compound of formula VII thus obtained according to step 7, by means of a reaction analogous to that of step 6 above, so as to replace the amino-protecting group $R_8$ with a hydrogen atom to give a compound of formula I according to the invention in which $R_4$ is a group —C(=$NR_5$)NHR'$_5$ and $R_5$ and R'$_5$ are each a hydrogen atom.

In a first variant, step 7 can be carried out as indicated below without effecting the deprotection of step 8:

7a) reacting the hydrochloride of a compound of formula I obtained in one of steps 4 or 6 above with a compound of the formula

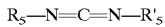

in which $R_5$ and R'$_5$ are each a linear, branched or cyclized $C_1$–$C_6$ alkly group, in an inert solvent, for example acetonitrile, at a temperature close to room temperature, for 4 to 48 hours, to give a compound of formula I according to the invention in which $R_5$ and R'5 are each a linear, branched or cyclized $C_1$–$C_6$ alkyl group and A is a single bond or the group —CO—$(CH_2)_p$—NH—.

In a second variant of step 7, the hydrochloride of a compound of formula VI obtained according to one of steps 4 or 6 above is reacted with a compound of the formula

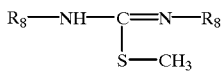

in which $R_8$ is an amino-protecting group of the Boc type, in the presence of an aprotic organic base such as triethylamine, and in the presence of mercuric oxide, in a solvent, for example ethanol, at room temperature, for 5 to 50 hours, to give the compound of formula VII, the structure of which is analogous to that obtained in step 7 above. This compound is then treated by the process described in step 8 above to give the compound of formula I according to the invention in which:

A is a single bond or a group —CO—$(CH_2)_p$—NH—, and
$R_4$ is the group —C(=NH)$NH_2$.

Some of the compounds of formulae III and IV, particularly the compounds referred to in claim 3 below, are novel products useful as synthesis intermediates and constitute one of the subjects of the invention.

The invention will be understood more clearly from the Preparatory Examples which follow and from the results of pharmacological tests obtained with some of the compounds according to the invention. In the case of compounds which have an asymmetric carbon in their structure, the absence of a particular indication, or the notation (R,S) [or (D,L) in the case of amino acids], means that the compounds are racemic; in the case of compounds which exhibit chirality, this is indicated immediately after the numbering of the substituent carried by said asymmetric carbon; the symbol (R) or (S) is then used in accordance with the Cahn-Ingold-Prelog rules or, in the case of amino acids, the notation (D) or (L) is used. The nomenclature used in the Examples is that recommended by Chemical Abstracts; thus, after reaction of the acid group with an amine, certain L-proline derivatives may become 2-(S)-pyrrolidinecarboxamide derivatives.

In the experimental section, the "Preparations" relate to the intermediates and the "Examples" relate to the products according to the invention.

The melting points (m.p.) indicated below are generally measured using a Koffler bench and are not corrected, so they represent instantaneous melting points.

PREPARATION I

3-Bromomethyl-2,4dichlorobenzenesulfonyl chloride 85.44 g (0.48 mol) of N-bromosuccinimide and then 200 mg of benzoyl peroxide are added to a solution, at room temperature, of 41.52 g (0.16 mol) of 2,4-dichloro-3-methylbenzenesulfonyl chloride in 150 ml of 1,1,2,2-tetrachloroethane. The reaction mixture is heated at 120° C. for 2 hours. It is cooled and filtered and the filtrate is washed successively with water, with saturated sodium bicarbonate solution and finally with water until the washings are neutral. The organic phase collected from the filtrate is then dried over magnesium sulfate and concentrated. Recrystallization from hexane gives 25.53 g of the expected product in the form of white crystals (yield =47%).
M.p.=90–92° C.

PREPARATION II

3-Chloromethyl-2,4-dichlorobenzenesulfonyl chloride 10 g (0.075 mol) of N-chlorosuccinimide and 30 mg of benzoyl peroxide are added to a solution of 6.5 g (0.025 mol) of 2,4-dichloro-3-methylbenzenesulfonyl chloride in 30 ml of 1,1,2,2-tetrachloroethane at room temperature and under a nitrogen atmosphere. The reaction mixture is heated at 120° C. for 3 hours, cooled to room temperature, poured into water and then extracted with dichloromethane. The organic phase is washed with water, with saturated sodium bicarbonate solution and finally with water until the washings are neutral. It is then dried over magnesium sulfate and concentrated under reduced pressure. Recrystallization from hexane gives 0.85 g of the expected product in the form of white crystals (yield=11.5%).
M.p. 68° C.

PREPARATION III

N-[(3-Bromomethyl-2,4-dichlorophenyl)sulfonyl]-(D,L)-proline methyl ester 27.08 g (0.08 mol) of the compound obtained according to Preparation I are added to a solution of 13.24 g (0.08 mol) of (D,L)-proline methyl ester hydrochloride in 60 ml of dichloromethane. The mixture is cooled to 0° C. and a solution of 23.3 ml (0.16 mol) of triethylamine in 20 ml of dichloromethane is added dropwise. The reaction mixture is then stirred at room temperature for 30 minutes. It is poured into water and extracted with dichloromethane. The organic phase is washed with 1 N hydrochloric acid solution and then with water until the pH is neutral. It is finally dried and concentrated under reduced pressure to give 34.48 g of an oil, which is used directly in the next steps. The product obtained also contains the compound N-[(3-chloromethyl-2,4-dichlorophenyl)sulfonyl]-(D,L)-proline methyl ester originating from a secondary reaction. As this by-product possesses essentially the same reactivity as the brominated derivative, the mixture is used directly without further purification.

PREPARATION IV

N-[(3-Bromomethyl-2,4-dichlorophenyl)sulfonyl]-L-proline methyl ester

The expected product is obtained in the form of an oil by following a procedure analogous to Preparation III, starting from L-proline methyl ester hydrochloride. (The product obtained contains the chlorinated analog originating from a secondary halogen exchange reaction.)

PREPARATION V

N-[(3-Bromomethyl-2,4dichlorophenyl)sulfonyl]-4-(trans)-hydroxy-L-proline methyl ester The expected product is obtained in the form of an oil by following a procedure analogous to Preparation III, starting from 4-(trans)-hydroxy-L-proline methyl ester hydrochloride. (The product obtained contains the chlorinated analog originating from a secondary halogen exchange reaction.)

PREPARATION VI

N-[[3-[(2-Methylquinolin-8-yl)oxymethy]-2,4-dichlorophenyl]sulfonyl]-D,L-proline methyl ester 0.051 g ($1.7.10^{-3}$ mol) of sodium hydride as an 80% suspension in oil is added to a solution of 0.270 g ($1.7.10^{-3}$ mol) of 8-hydroxy-2-methylquinoline in 5 ml of N,N-dimethylformnamide (DMF). After stirring for ten minutes at room temperature, a solution of 0.8 g of the compound obtained according to Preparation III in 2 ml of DMF is added. Stirring is maintained for 2 hours at room temperature. The reaction mixture is diluted with water and extracted with ethyl acetate. The organic phases are washed with water, dried over sodium sulfate, filtered and concentrated under reduced pressure. The residue obtained is purified by chromatography on silica gel using a toluene/ethyl acetate mixture (80/20; v/v) as the eluent. The solid recovered is recrystallized from 15 ml of isopropanol to give 0.7 g of the expected product in the form of a white powder (yield=81%).
M.p.=142° C.

PREPARATION VII

N-[[3-[(2-Methylquinolin-8-yl)oxymethyl]-2,4-dichlorophenyl]sulfonyl]-L-proline methyl ester By following a procedure analogous to Preparation VI, starting from the compound obtained according to Preparation IV, the expected product is obtained with a yield of 83% after recrystallization from isopropanol.
M.p.=136° C.
$[\alpha]_D^{23}$=+29.4° (c=1.01; CHCl$_3$)

PREPARATION VIII

N-[[3-[(2,4-Dimethylquinolin-8-yl)oxymethyl]-2,4-dichlorophenyl]sulfonyl]-L-proline methyl ester By following a procedure analogous to Preparation VI, starting from the compound obtained according to Preparation IV and 2,4-dimethyl-8-hydroxyquinoline, the expected product is obtained with a yield of 72% after recrystallization from isopropanol.
M.p.=138° C.
$[\alpha]_D^{22}$=−28° (c=0.5; CHCl$_3$)

PREPARATION IX

N-[[3-[(2,4-Dimethylquinolin-8-yl)oxymethyl]-2,4-dichlorophenyl]sulfonyl]-4-(trans)-hydroxy-L-proline methyl ester By following a procedure analogous to Preparation VI, starting from the compound obtained according to Preparation V and 2,4-dimethyl-8-hydroxyquinoline, the expected product is obtained with a yield of 44% in the form of a white solid after purification by chromatography on silica gel using a dichloromethane/ethyl acetate mixture (7/3; v/v) as the eluent, followed by crystallization from isopropyl ether.
M.p.=100° C.
$[\alpha]_D^{21}$=−30° (c=0.31; CHCl$_3$)

PREPARATION X

N-[[3-[(2-Methylquinolin-8-yl)oxymethyl]-2,4-dichlorophenyl]sulfonyl]-D,L-proline 20 ml ($20.10^{-3}$ mol) of 1 N aqueous sodium hydroxide solution are added to a solution of 5.14 g ($10.2.10^{-3}$ mol) of the compound obtained according to Preparation VI in 100 ml of 1,2-dimethoxyethane. The reaction mixture is stirred at 40° C. for 1.5 hours and then at room temperature for 20 hours. The mixture is then concentrated under reduced pressure and the residue is taken up with water and acidified to pH 5 with 1 N hydrochloric acid. After extraction with dichloromethane, the organic phase is washed with water, dried and concentrated under reduced pressure. The resulting solid is recrystallized from 30 ml of isopropanol to give 4.4 g of the expected product in the form of white crystals (yield=87%).
M.p.=120° C.

PREPARATION XI

N-[[3-[(2-Methylquinolin-8yl)oxymethyl]-2,4-dichlorophenyl]sulfonyl]-L-proline

The expected product is obtained with a yield of 93% by following a procedure analogous to Preparation X, starting from the compound obtained according to Preparation VII.
M.p.=135° C.
$[\alpha]_D^{23}$=−99.3° (c=0.31; CHCl$_3$)

PREPARATION XII

N-[[3-[(2,4-Dimethylquinolin-8-yl)oxymethyl]-2,4-dichlorophenyl]sulfonyl]-L-proline The expected product is obtained with a yield of 95% by following a procedure analogous to Preparation X starting from the compound obtained according to Preparation VIII.
M.p.=219–220° C.
$[\alpha]_D^{22}$=−79.2° (c=0.31; CHCl$_3$)

PREPARATION XIII

N-[[3-[(2,4-Dimethylquinolin-8-yl)oxymethyl]-2,4-dichloropheny]sulfonyl]-4-(trans)-hydroxy-L-proline A suspension of 0.53 g (0.983.10$^{-3}$ mol) of the compound obtained according to Preparation IX in 35 ml of methanol is prepared, 5 ml of 0.3 N sodium hydroxide solution are added and the reaction mixture is stirred for 18 hours under reflux. It is then concentrated under reduced pressure and the residue is then taken up with water and acidified to pH 5 with 1 N hydrochloric acid. After extraction with dichloromethane, the organic phase is washed with water, dried over magnesium sulfate and then concentrated under reduced pressure to give 490 mg of the expected product in the form of a white solid.
M.p.>260° C.
$[\alpha]_D^{21}$=−55° (c=0.36; CHCl$_3$)

REPARATION XIV

1-[[3-[(2-Methylquinolin-8-yl)oxymethyl]-2,4-dichlorophenyl]sulfonyl]-N-[2-(1,1-dimethylethoxycarbonylamino)ethyl]-N-methyl-2-(S)-pyrrolidinecarboxamide A solution of 0.742 g (1.5.10$^{-3}$ mol) of the acid obtained according to Preparation XI in 10 ml of dichloromethane is prepared and 0.21 g (1.1.10$^{-3}$ mol) of 1-(3-dimethylaminopropyl)-3-ethylcarbodiimide (EDCI) hydrochloride, 0.15 g (1.1.10$^{-3}$ mol) of 1-hydroxy-7-azabenzotriazole (HOAT) and then 0.261 g (1.5.10$^{-3}$ mol) of N-methyl-N'-(1,1-dimethylethoxycarbonyl)-1,2-ethanediamine are added. The reaction mixture is stirred at room temperature for 20 hours and then concentrated under reduced pressure. The residue obtained is purified by chromatography on silica gel using a toluene/isopropanol mixture (95/5; v/v) as the eluent to give 0.61 g of the expected product in the form of a white solid with a yield of 61%.
M.p.=88° C.
$[\alpha]_D^{22}$=−4.5° (c=0.2; CH$_3$OH)

PREPARATION XV

1-[[3-[(2-Methylquinolin-8-yl)oxymethyl]-2,4-dichlorophenyl]sulfonyl]-N-[3-(1,1-dimethylethoxycarbonylamino)propyl]-2-(S)-pyrrolidinecarboxamide The expected product is obtained with a yield of 57% by following a procedure analogous to Preparation XIV, starting from N-(1,1-dimethylethoxycarbonyl)-1,3-propanediamine.
M.p.=78–80° C.
$[\alpha]_D^{22}$=−38° (c=0.3; CH$_3$OH)

PREPARATION XVI

1-[[3-[(2-Methylquinolin-8-yl)oxymethyl]-2,4-dichlorophenyl]sulfonyl]-N-[[1-(1,1-dimethylethoxycarbonyl)piperidin-4-yl]methyl]-2-(S)-pyrrolidinecarboxamide The expected product is obtained with a yield of 20% by following a procedure analogous to Preparation XIV, starting from 1-(1,1-dimethylethoxycarbonyl)-4-(aminomethyl)piperidine.
M.p.=68° C.
$[\alpha]_D^{22}$=+38° (c=0.32; CH$_3$OH)

PREPARATION XVII

1-[[3-[(2-Methylquinolin-8-yl)oxymethyl]-2,4-dichlorophenyl]sulfonyl]-N-[1-(1,1-dimethylethoxycarbonyl)piperidin-4-yl]-2-(S)-pyrrolidinecarboxamide The expected product is obtained with a yield of 42.3% by following a procedure analogous to Preparation XIV, starting from 1-(1,1-dimethylethoxycarbonyl)-4-aminopiperidine.
M.p.=70–74° C.
$[\alpha]_D^{22}$=−27° (c=0.37; CH$_3$OH)

PREPARATION XVII

1-[[3-[(2-Methylquinolin-8-yl)oxymethyl]-2,4-dichlorophenyl]sulfonyl]-2-(S)-pyrrolidinecarboxylic acid 1-(1,1-dimethylethoxycarbonyl)piperidin-4-yl ester The expected product is obtained in the form of an oil with a yield of 23.6% by following a procedure analogous to Preparation XIV, starting from 1-(1,1-dimethylethoxycarbonyl)-4-hydroxypiperidine.
$[\alpha]_D^{22}$=+22° (c=0.17; CH$_3$OH)

PREPARATION XIX

1-[[3-[(2-Methylquinolin-8-yl)oxymethyl]-2,4-dichlorophenyl]sulfonyl]-2-(S)-pyrrolidinecarboxylic acid [1-(1,1-dimethylethoxycarbonyl)piperidin-4-yl-methyl] ester The expected product is obtained with a yield of 37.6% by following a procedure analogous to Preparation XIV, starting from 1-(1,1-dimethylethoxycarbonyl)-4-hydroxymethylpiperidine.
M.p.=66–68° C.
$[\alpha]_D^{22}$=−19° (c=0.28; CH$_3$OH)

PREPARATION XX

1-[[3-[(2,4-Dimethylquinolin-8-yl)oxymethyl]-2,4-dichlorophenyl]sulfonyl]-N-[(1,1-dimethylethoxycarbonylamino)propyl]-2-(S)-pyrrolidinecarboxamide The expected product is obtained with a yield of 74% by following a procedure analogous to Preparation XIV, starting from the compound of Preparation XII and N-(1,1-dimethylethoxycarbonyl)-1,3-propanediamine.

M.p.=80–84° C.
$[\alpha]_D^{22}=-38°$ (c=0.32; CH$_3$OH)

PREPARATION XXI

1-[[3-[(2,4-Dimethylquinolin-8-yl)oxymethyl]-2,4-dichlorophenyl]sulfonyl]-2-(S)-[[4-(1,1-dimethylethoxycarbonyl)piperazin-1-yl]carbonyl]pyrrolidine The expected product is obtained with a yield of 66% by following a procedure analogous to Preparation XX, starting from 1-(1,1-dimethylethoxycarbonyl)piperazine.
M.p.=100° C.
$[\alpha]_D^{24}=-33.3°$ (c=0.30; CH$_3$OH)

PREPARATION XXII

1-[[3-[(2,4-Dimethylquinolin-8-yl)oxymethyl]-2,4dichlorophenyl]sulfonyl]-2-(S)-[[4-(1,1-dimethylethoxycarbonyl)piperazin-1-yl]carbonyl]-4-(R)-hydroxypyrrolidine The expected product is obtained with a yield of 72% by following a procedure analogous to Preparation XXI, starting from the compound of Preparation XIII.
M.p.=223° C.
$[\alpha]_D^{21}=-33°$ (c=0.34; CHCl$_3$)

EXAMPLE 1

1-[[3-[(2-Methylquinolin-8-yl)oxymethyl]-2,4-dichlorophenyl]sulfonyl]-2-(S)-[(3,5-dimethylpiperazin-1-yl)carbonyl]pyrrolidine The expected product is obtained with a yield of 13% by following a procedure analogous to Preparation XIV, starting from an excess of 2,6-dimethylpiperazine.
M.p.=102–106° C.
$[\alpha]_D^{22}=-2°$ (c=0.3; CHCl$_3$)

EXAMPLE 2

1-[[3-[(2-Methylquinolin-8-yl)oxymethyl]-2,4-dichlorophenyl]sulfonyl]-2-(S)-[(piperazin-1-yl)carbonyl]pyrrolidine The expected product is obtained with a yield of 20% by following a procedure analogous to Preparation XIV, starting from an excess of piperazine.
M.p.=164–166° C.
$[\alpha]_D^{24}=-1°$ (c=0.28; CHCl$_3$)

EXAMPLE 3

1-[[3-[(2-Methylquinolin-8-yl)oxymethyl]-2,4-dichlorophenyl]sulfonyl]-N-(2-aminoethyl)-2-(S)-pyrrolidinecarboxamide The expected product is obtained with a yield of 40.9% by following a procedure analogous to Preparation XIV, starting from an excess of 1,2-ethanediamine.
M.p.=78–80° C.
$[\alpha]_D^{21}=-58.6°$ (c=0.35; CHCl$_3$)

EXAMPLE 4

1-[[3-[(2,4-Dimethylquinolin-8-yl)oxymethyl]-2,4-dichlorophenyl]sulfonyl]-N-(2-aminoethyl)-2-(S)-pyrrolidinecarboxamide The expected product is obtained with a yield of 42.7% by following a procedure analogous to Preparation XX, starting from an excess of 1,2-ethanediamine.
M.p.=104–106° C.
$[\alpha]_D^{21}=-55.2°$ (c=0.28; CHCl$_3$)

EXAMPLE 5

1-[[3-[(2,4-Dimethylquinolin-8-yl)oxymethyl]-2,4-dichlorophenyl]sulfonyl]-2-(S)-[(piperazin-1-yl)carbonyl]pyrrolidine bistrifluoroacetate A mixture of 0.6 g (0.885.10$^{-3}$ mol) of the compound obtained according to Preparation XXI and 96 mg (0.885.10$^{-3}$ mol) of anisole is prepared and 3 ml of trifluoroacetic acid are then added at 0° C. The solution is stirred for 3 hours at 0° C. and then overnight at room temperature. After concentration under reduced pressure, the residue is precipitated in anhydrous diethyl ether. The precipitate is separated off, rinsed with ether and dried under vacuum to give 0.64 g of the expected product in the form of a white solid (yield=90%).
M.p.=150° C.
$[\alpha]_D^{24}=+12.6°$ (c=0.31; CH$_3$OH)

EXAMPLE 6

1-[[3-[(2-Methylquinolin-8-yl)oxymethyl]-2,4-dichlorophenyl]sulfonyl]-N-methyl-N-(2-aminoethyl)-2-(S)-pyrrolidinecarboxamide bistrifluoroacetate The expected product is obtained with a yield of 95% by following a procedure analogous to Example 5, starting from the compound obtained according to Preparation XIV.
M.p.=130° C.
$[\alpha]_D^{22}=+3.2°$ (c=0.5; CH$_3$OH)

EXAMPLE 7

1-[[3-[(2,4-Dimethylquinolin-8-yl)oxymethyl]-2,4-dichlorophenyl]sulfonyl]-4-(R)-hydroxy-2-(S)-[(piperazin-1-yl)carbonyl]pyrrolidine bistrifluoroacetate The expected product is obtained with a yield of 92% by following a procedure analogous to Example 5, starting from the compound obtained according to Preparation XXII.
M.p.=165° C.
$[\alpha]_D^{23}=+19°$ (c=0.32; CH$_3$OH)

EXAMPLE 8

1-[[3-[(2-Methylquinolin-8-yl)oxymethyl]-2,4-dichlorophenyl]sulfonyl]-N-(piperidin-4-yl)-2-(S)-pyrrolidinecarboxamide dihydrochloride 50 ml of a 1.25 N solution of hydrogen chloride in ethyl acetate are prepared and then mixed with 8.25 g (12.17.10$^{-3}$ mol) of the compound obtained according to Preparation XVII. The reaction medium is stirred for 15 hours at room temperature. The precipitate obtained is filtered off, washed with ether and then dried and redissolved in distilled water. After lyophilization of the resulting solution, 7.11 g of the expected product are obtained in the form of a white solid (yield =95%).
M.p.=177° C.
$[\alpha]_D^{22}=-21°$ (c=0.33; CH$_3$OH)

EXAMPLE 9

1-[[3-[(2-Methylquinolin-8-yl)oxymethyl]-2,4-dichlorophenyl]sulfonyl]-N-(3-aminopropyl)-2-(S)-pyrrolidinecarboxamide dihydrochloride The expected product is obtained with a yield of 68% by following a procedure analogous to Example 8, starting from the compound obtained according to Preparation XV.

M.p.=158–162° C.
$[\alpha]_D^{22}$=−36° (c=0.29; CH$_3$OH)

EXAMPLE 10

1-[[3-[(2-Methylquinolin-8-yl)oxymethyl]-2,4-dichlorophenyl]sulfonyl]-N-[(piperidin-4-yl)methyl]-2-(S)-pyrrolidinecarboxamide dihydrochloride The expected product is obtained with a yield of 59% by following a procedure analogous to Example 8, starting from the compound obtained according to Preparation XVI.
M.p.=170° C.
$[\alpha]_D^{22}$=−27° (c=0.26; CH$_3$OH)

EXAMPLE 11

1-[[3-[(2-Methylquinolin-8-yl)oxymethyl]-2,4-dichlorophenyl]sulfonyl]-2-(S)-pyrrolidinecarboxylic acid piperidin-4-yl ester dihydrochloride The expected product is obtained with a yield of 92% by following a procedure analogous to Example 8, starting from the compound obtained according to Preparation XVIII.
M.p.=150–154° C.
$[\alpha]_D^{22}$=+11° (c=0.3; CH$_3$OH)

EXAMPLE 12

1-[[3-(2-Methylquinolin-8-yl)oxymethyl]-[2,4-dichlorophenyl]sulfonyl]-2-(S)-pyrrolidinecarboxylic acid [(piperidin-4-yl)methyl] ester dihydrochloride The expected product is obtained with a yield of 95% by following a procedure analogous to Preparation XXX, starting from the compound obtained according to Preparation XIX.
M.p.=154–158° C.
$[\alpha]_D^{22}$=+7° (c=0.31; CH$_3$OH)

EXAMPLE 13

1-[[3-[(2,4-Dimethylquinolin-8-yl(oxymethyl]-2,4-dichlorophenyl]sulfonyl]-N-(3-aminopropyl)-2-(S)-pyrrolidinecarboxamide dihydrochloride The expected product is obtained with a yield of 68% by following a procedure analogous to Example 8, starting from the compound obtained according to Preparation XX.
M.p.=158–162° C.
$[\alpha]_D^{22}$=−36° (c=0.29; CH$_3$OH)

PREPARATION XXIII

1-[[3-[(2,4-Dimethylquinolin-8-yl)oxymethyl]-2,4-dichlorophenyl]sulfonyl]-2-(S)-[[4-[[(1,1-dimethylethoxycarbonylamino]-[(1,1-dimethylethoxycarbonyl)imino]methyl]piperazin-1-yl]carbonyl]pyrrolidine a) A solution of 0.475 g of the compound obtained according to Example 5 is treated with 1 N sodium hydroxide solution in order to bring the pH to a slightly basic value, and extraction is carried out twice with ethyl acetate. The combined organic phases are dried over magnesium sulfate and concentrated under reduced pressure to give the compound corresponding to Example 5 in the form of the base.

b) A mixture of 0.34 g (0.589.10$^{-3}$ mol) of the compound obtained above, 0.131 g (1.3.10$^{-3}$ mol) of triethylamine and 0.17 g (0.589.10$^{-3}$ mol) of N,N'-bis(1,1-dimethylethoxycarbonyl)thiourea in 10 ml of DMF is prepared. It is cooled to 0° C., 0.18 g (0.65.10$^{-3}$ mol) of mercuric chloride is added and the reaction mixture is then stirred for 3 hours at room temperature. It is then diluted with 60 ml of ethyl acetate and washed with water. The organic phase is dried and then concentrated under reduced pressure. The residue is purified by chromatography on silica gel using a dichloromethane/ethyl acetate mixture (614; v/v) as the eluent to give 0.38 g of the expected product in the form of a white solid (yield 79%).
M.p.=100° C.
$[\alpha]_D^{24}$=−25° (c=0.29; CH$_3$OH)

PREPARATION XXIV

1-[[3-[(2-Methylquinolin-8-yl)oxymethyl]-2,4-dichlorophenyl]sulfonyl]-2-(S)-[[4-[[(1,1-dimethylethoxycarbonyl)amino]-[(1,1-dimethylethoxycarbonyl)imino]methyl]piperazin-1-yl]carbonyl]pyrrolidine The expected product is obtained with a yield of 70% by following a procedure analogous to Preparation XXIII, starting from the compound obtained according to Example 2.
M.p.=164–168° C.
$[\alpha]_D^{23}$=+2° (c=0.26; CH$_3$OH)

PREPARATION XXV

1-[[3-[(2-Methylquinolin-8-yl)oxymethyl]-2,4-dichlorophenyl]sulfonyl]-2-(S)-[[4-[[(1,1-dimethylethoxycarbonyl)amino]-[(1,1-dimethylethoxycarbonyl)imino]methyl]-3,5-dimethylpiperazin-1-yl]carbonyl]pyrrolidine The expected product is obtained with a yield of 53% by following a procedure analogous to Preparation XXIII, starting from the compound obtained according to Example 1.

PREPARATION XXVI

1-[[3-[(2,4-Dimethylquinolin-8-yl)oxymethyl]-2,4-dichlorophenyl]sulfonyl]-2-(S)-[[4-[[(1,1-dimethylethoxycarbonyl)amino]-[(1,1-dimethylethoxycarbonyl)imino]methyl]piperazin-1-yl]carbonyl]-4-(R)-hydroxypyrrolidine The expected product is obtained with a yield of 77%, after crystallization from isopropyl ether, by following a procedure analogous to Preparation XXIII, starting from the compound obtained according to Example 7.
M.p.=200° C.
$[\alpha]_D^{21}$=−138° (c=0.33; CHCl$_3$)

REPARATION XXVII

1-[[3-[(2-Methylquinolin-8-yl)oxymethyl]-2,4-dichlorophenyl]sulfonyl]-N-[2-[[(1,1-dimethylethoxycarbonyl)amino]-[(1,1-dimethylethoxycarbonyl)imino]-methylamino]ethyl]-2-(S)-pyrrolidinecarboxamide The expected product is obtained with a yield of 50% by following a procedure analogous to Preparation XXIII, starting from the compound obtained according to Example 3.

PREPARATION XXVIII

1-[[3-[(2,4-Dimethylquinolin-8-yl)oxymethyl]-2,4-dichlorophenyl]sulfonyl]-N-[2-[[(1,1-dimethylethoxycarbonyl)amino]-[(1,1-dimethylethoxycarbonyl)imino]methylamino]ethyl]-2-(S)-pyrrolidinecarboxamide The expected product is obtained with a yield of 51% by following a procedure analogous to Preparation XXIII, starting from the compound obtained according to Example 4.

M.p.=114–118° C.
$[\alpha]_D^{23}$=−24° (c=0.4; $CH_3OH$)

PREPARATION XXIX

1-[[3-[(2,4-Dimethylquinolin-8-yl)oxymethyl]-2,4-dichlorophenyl]sulfonyl]-N-[3-[[(1,1-dimethylethoxycarbonyl)amino]-[(1,1-dimethylethoxycarbonyl)imino]methylamino]propyl]-2-(S)-pyrrolidinecarboxamide The expected product is obtained with a yield of 70% by following a procedure analogous to Preparation XXIII, starting from the compound obtained according to Example 13.

M.p.=106–110° C.
$[\alpha]_D^{22}$=−20° (c=0.33; $CH_3OH$)

PREPARATION XXX

1-[[3-[(2-Methylquinolin-8-yl)oxymethyl]-2,4-dichlorophenyl]sulfonyl]-N-[3-[[(1,1-dimethylethoxycarbonyl)amino]-[(1,1-dimethylethoxycarbonyl)imino]-methylamino]propyl]-2-(S)-pyrrolidinecarboxamide The expected product is obtained with a yield of 30% by following a procedure analogous to Preparation XXIII, starting from the compound obtained according to Example 9.

M.p.=116–120° C.
$[\alpha]_D^{23}$=−17° (c=0.31; $CH_3OH$)

PREPARATION XXXI

1-[[3-[(2-Methylquinolin-8-yl)oxymethyl]-2,4-dichlorophenyl]sulfonyl]-N-[2-[[(1,1-dimethylethoxycarbonyl)amino]-[(1,1-dimethylethoxycarbonyl)imino]-methylamino]ethyl]-N-methyl-2-(S)-pyrrolidinecarboxamide The expected product is obtained with a yield of 68% by following a procedure analogous to Preparation XXIII, starting from the compound obtained according to Example 6.

M.p.=95° C.
$[\alpha]_D^{22}$=−10.4° (c=0.45; $CHCl_3$)

PREPARATION XXXII

1-[[3-[(2-Methylquinolin-8-yl)oxymethyl]-2,4-dichlorophenyl]sulfonyl]-N-[[1-[[(1,1-dimethylethoxycarbonyl)amino]-[(1,1-dimethylethoxycarbonyl)imino]-methyl]piperidin-4-yl]methyl]-2-(S)-pyrrolidinecarboxamide The expected product is obtained with a yield of 58% by following a procedure analogous to Preparation XXIII, starting from the compound obtained according to Example 10.

M.p.=104–108° C.
$[\alpha]_D^{22}$=−32° (c=0.30; $CH_3OH$)

PREPARATION XXXIII

1-[[3-[(2-Methylquinolin-8-yl)oxymethyl]-2,4-dichlorophenyl]sulfonyl]-N-[1-[[(1,1-dimethylethoxycarbonyl)amino]-[(1,1-dimethylethoxycarbonyl)imino]-methyl]piperidin-4-yl]-2-(S)-pyrrolidinecarboxamide The expected product is obtained with a yield of 47.3% by following a procedure analogous to Preparation XXIII, starting from the compound obtained according to Example 8.

PREPARATION XXXIV

1-[[3-[(2-Methylquinolin-8-yl)oxymethyl]-2,4-dichlorophenyl]sulfonyl]-2-(S)-pyrrolidinecarboxylic acid [1-[[(1,1-dimethylethoxycarbonyl)amino]-[(1,1-dimethylethoxycarbonyl)imino]methyl]piperidin-4-yl] ester The expected product is obtained with a yield of 80% by following a procedure analogous to Preparation XXIII, starting from the compound obtained according to Example 11.

M.p.=75° C.
$[\alpha]_D^{22}$=+23° (c=0.25; $CH_3OH$)

PREPARATION XXXV

1-[[3-[(2-Methylquinolin-8yl)oxymethyl]-2,4-dichlorophenyl]sulfonyl]-2-(S)-pyrrolidinecarboxylic acid [[1-[[(1,1-dimethylethoxycarbonyl)amino]-[(1,1-dimethylethoxycarbonyl)imino]methyl]piperidin-4-yl]methyl] ester The expected product is obtained with a yield of 57% by following a procedure analogous to Preparation XXIII, starting from the compound obtained according to Example 12.

M.p.=74° C.
$[\alpha]_D^{22}$=−19° (c=0.29; $CH_3OH$)

EXAMPLE 14

1-[[3-[(2,4-Dimethylquinolin-8-yl)oxymethyl]-2,4-dichlorophenyl]sulfonyl]-2-(S)-[[4-(aminoiminomethyl)piperazin-1-yl]carbonyl]pyrrolidine bistrifluoroacetate The expected product is obtained by following a procedure analogous to the process for obtaining the compound according to Example 5, starting from the compound of Preparation XXIII. It is then redissolved in pure water, the solution is filtered and the filtrate is lyophilized to give the expected product pure in the form of a cottony white solid (yield =79%).

M.p.=145° C.
$[\alpha]_D^{24}$=+14° (c =0.34; $CH_3OH$)

EXAMPLE 15

1-[[3-[(2,4-Dimethylquinolin-8-yl)oxymethyl]-2,4-dichlorophenyl]sulfonyl]-2-(S)-[[4-(aminoiminomethyl)piperazin-1-yl]carbonyl]-4-(R)-hydroxypyrrolidine bistrifluoroacetate The expected product is obtained with a yield of 87% by following a procedure analogous to the process of Example 14, starting from the compound obtained according to Preparation XXVI.

M.p.=165° C.
$[\alpha]_D^{21}$=+39° (c=0.31; $CH_3OH$)

EXAMPLE 16

1-[[3-[(2-Methylquinolin-8-yl)oxymethyl]-2,4-dichlorophenyl]sulfonyl]-N-[2-[(aminoiminomethyl)amino]ethyl]-2-(S)-pyrrolidinecarboxamide bistrifluoroacetate The expected product is obtained with a yield of 52% by following a procedure analogous to Example 14, starting from the compound of Preparation XXVII.

M.p.=138–142° C.
$[\alpha]_D^{23}$=–16° (c=0.30; $CH_3OH$)

EXAMPLE 17

1-[[3-[(2-Methylquinolin-8-yl)oxymethyl]-2,4-dichlorophenyl]sulfonyl]-N-[2-[(aminoiminomethyl)amino]ethyl]-N-(methyl)-2-(S)-pyrrolidinecarboxamide bistrifluoroacetate The expected product is obtained with a yield of 88% by following a procedure analogous to Example 14, starting from the compound of Preparation XXXI.
M.p.=137° C.
$[\alpha]_D^{22}$=+10.6° (c=0.48; $CH_3OH$)

EXAMPLE 18

1-[[3-[(2-Methylquinolin-8-yl)oxymethyl]-2,4-dichlorophenyl]sulfonyl]-2-(S)-pyrrolidinecarboxylic acid [[1-(aminoiminomethyl)piperidin-4-yl]methyl] ester bistrifluoroacetate The expected product is obtained with a yield of 70% by following a procedure analogous to Example 14, starting from the compound obtained according to Preparation XXXV.
M.p.=126–130° C.
$[\alpha]_D^{22}$=–1° (c=0.38; $CH_3OH$)

EXAMPLE 19

1-[[3-[(2,4-Dimethylquinolin-8yl)oxymethyl]-2,4-dichlorophenyl]sulfonyl]-N-[2-[(aminoiminomethyl)amino]ethyl]-2-(S)-pyrrolidinecarboxamide dihydrochloride The expected product is obtained with a yield of 60% by following a procedure analogous to the process for obtaining the compound according to Example 8, starting from the compound obtained according to Preparation XXVIII.
M.p.=170–174° C.
$[\alpha]_D^{24}$=–39° (c=0.30; $CH_3OH$)

EXAMPLE 20

1-[[3-[(2,4-Dimethylquinolin-8-yl)oxymethyl]-2,4-dichlorophenyl]sulfonyl]-N-[3-[(aminoiminomethyl)amino]propyl]-2-(S)-pyrrolidinecarboxamide dihydrochloride The expected product is obtained with a yield of 80% by following a procedure analogous to Example 19, starting from the compound obtained according to Preparation XXIX.
M.p.=170–174° C.
$[\alpha]_D^{24}$=–34° (c=0.29; $CH_3OH$)

EXAMPLE 21

1-[[3-[(2-Methylquinolin-8-yl)oxymethyl]-2,4-dichlorophenyl]sulfonyl]-N-[3-[(aminoiminomethyl)amino]propyl]-2-(S)-pyrrolidinecarboxamide dihydrochloride The expected product is obtained with a yield of 52% by following a procedure analogous to Example 19, starting from the compound obtained according to Preparation XXX.
M.p.=158–160° C.
$[\alpha]_D^{22}$=–30° (c =0.31; $CH_3OH$)

EXAMPLE 22

1-[[3-[(2-Methylquinolin-8-yl)oxymethyl]-2,4-dichlorophenyl]sulfonyl]-N-[[1-(aminoiminomethyl)piperidin-4-yl]methyl]-2-(S)-pyrrolidinecarboxamide dihydrochloride The expected product is obtained with a yield of 95% by following a procedure analogous to Example 19, starting from the compound obtained according to Preparation XXXII.
M.p.=190–192° C.
$[\alpha]_D^{22}$=–27° (c=0.35; $CH_3OH$)

EXAMPLE 23

1-[[3-[(2-Methylquinolin-8-yl)oxymethyl]-2,4-dichlorophenyl]sulfonyl]-N-[1-(aminoiminomethyl)piperidin-4-yl]-2-(S)-pyrrolidinecarboxamide dihydrochloride The expected product is obtained with a yield of 47% by following a procedure analogous to Example 19, starting from the compound obtained according to Preparation XXXIII.
M.p.=152–156° C.
$[\alpha]_D^{22}$=–17° (c=0.30; $CH_3OH$)

EXAMPLE 24

1-[[3-[(2-Methylquinolin-8-yl)oxymethyl]-2,4-dichlorophenyl]sulfonyl]-2-(S)-[[4-(aminoiminomethyl)piperazin-1-yl]carbonyl]pyrrolidine dihydrochloride The expected product is obtained with a yield of 60% by following a procedure analogous to Example 19, starting from the compound obtained according to Preparation XXIV.
M.p.=176–180° C.
$[\alpha]_D^{25}$=+19° (c=0.28; $CH_3OH$)

EXAMPLE 25

1-[[3-[(2-Methylquinolin-8yl)oxymethyl]-2,4-dichlorophenyl]sulfonyl]-2-(S)-[[4-(aminoiminomethyl)-3,5-dimethylpiperazin-1-yl]carbonyl]pyrrolidine dihydrochloride The expected product is obtained with a yield of 70% by following a procedure analogous to Example 19, starting from the compound obtained according to Preparation XXV.
M.p.=186–190° C.
$[\alpha]_D^{22}$=+21° (c =0.35; $CH_3OH$)

EXAMPLE 26

1-[[3-[(2-Methylquinolin-8-yl)oxymethyl]-2,4-dichlorophenyl]sulfonyl]-2-(S)-pyrrolidinecarboxylic acid [1-(aminoiminomethyl)piperidin-4-yl] ester dihydrochloride The expected product is obtained with a yield of 96% by following a procedure analogous to Example 19, starting from the compound obtained according to Preparation XXXIV.
M.p.=180–184° C.
$[\alpha]_D^{22}$=–11° (c=0.30; $CH_3OH$)

EXAMPLE 27

1-[[3-[(2-Methylquinolin-8-yl)oxymethyl]-2,4-dichlorophenyl]sulfonyl]-2-(S)-[[4-[(1-methylethylamino)(1-methylethylimino)methyl]piperazin-1-yl]-carbonyl]pyrrolidine dihydrochloride a) A solution of 0.24 g ($0.426.10^{-3}$ mol) of the compound obtained according to Example 2 in 5 ml of methanol is prepared and 0.18 ml of an approximately 5 M solution of hydrogen chloride in methanol is added gradually. The mixture is stirred for 1 hour at room temperature and the solvent is then driven off under reduced pressure. The residue is triturated in the presence of ethyl ether and the crystals obtained are filtered off and dried to give 0.24 g of the hydrochloride of the starting material in the form of yellow crystals.

b) A suspension of 0.24 g ($0.38.10^{-3}$ mol) of the compound obtained above in 15 ml of acetonitrile is prepared, 0.24 g ($1.9.10^{-3}$ mol) of diisopropylcarbodiimide is added and the mixture is stirred at room temperature for 24 hours. The solvent is then evaporated off under reduced pressure and the residue is washed several times with hot ethyl acetate. After drying of the crystals under vacuum, 90 mg of the expected product are obtained in the form of white crystals (yield=31%).
M.p.=148–150° C.
$[\alpha]_D^{22}$=−1° (c=0.30; $CH_3OH$)

EXAMPLE 28

1-[[3-[(2-Methylquinolin-8-yl)oxymethyl]-2,4-dichlorophenyl]sulfonyl]-2-(S)-[[4-[(cyclohexylamino)(cyclohexylimino)methyl]piperazin-1-yl]carbonyl]-pyrrolidine dihydrochloride The expected product is obtained with a yield of 26% by following a procedure analogous to the process of Example 27, starting from dicyclohexylcarbodiimide.
M.p.=174–178° C.
$[\alpha]_D^{22}$=+9° (c=0.28; $CH_3OH$)

PREPARATION XXXVI

1-[[3-[(2-Methylquinolin-8-yl)oxymethyl]-2,4-dichlorophenyl]sulfonyl]-N-[4-(1,1-dimethylethoxycarbonylamino)butyl]-2-(S)-pyrrolidinecarboxamide The expected product is obtained with a yield of 70% by following a procedure analogous to Preparation XIV, starting from N-(1,1-dimethylethoxycarbonyl)-1,4-butanediamine.
M.p.=72–74° C.
$[\alpha]_D^{22}$=−48° (c=0.29; $CHCl_3$)

PREPARATION XXXVII

1-[[3-[(2-Methylquinolin-8-yl)oxymethyl]-2,4-dichlorophenyl]sulfonyl]-N-[2-[1-(1,1-dimethylethoxycarbonyl)piperidin-4-yl]ethyl]-2-(S)-pyrrolidinecarboxamide The expected product is obtained with a yield of 60% by following a procedure analogous to Preparation XIV, starting from 1-(1,1-dimethylethoxycarbonyl)-4-(2-aminoethyl)piperidine.
M.p.=105° C.
$[\alpha]_D^{22}$=−35° (c=0.97; $CH_3OH$)

PREPARATION XXXVIII

1-[[3-[(2,4-Dimethylquinolin-8-yl)oxymethyl]-2,4-dichlorophenyl]sulfonyl]-N-[[1-(1,1-dimethylethoxycarbonyl)piperidin-4-yl]methyl]-2-(S)-pyrrolidinecarboxamide The expected product is obtained with a yield of 60% by following a procedure analogous to Preparation XIV, starting from the acid obtained according to Preparation XII and 1-(1,1-dimethylethoxycarbonyl)-4-(aminomethyl)piperidine.
M.p.=80° C.
$[\alpha]_D^{26}$=−37° (c=1.05; $CH_3OH$)

PREPARATION XXXIX

1-[[3-[(2,4-Dimethylquinolin-8-yl)oxymethyl]-2,4-dichlorophenyl]sulfonyl]-N-[1-(1,1-dimethylethoxycarbonyl)piperidin-4-yl]-2-(S)-pyrrolidinecarboxamide The expected product is obtained with a yield of 54% by following a procedure analogous to Preparation XXXVIII, starting from 1-(1,1-dimethylethoxycarbonyl)-4-aminopiperidine.
M.p.=60–64° C.
$[\alpha]_D^{25}$=−21° (c=1.32; $CH_3OH$)

EXAMPLE 29

1-[[3-[(2-Methylquinolin-8-yl)oxymethyl]-2,4-dichlorophenyl]sulfonyl]-N-(4-aminobutyl)-2-(S)-pyrrolidinecarboxamide dihydrochloride 2.7 g ($4.10^{-3}$ mol) of the compound obtained according to Preparation XXXVI are added to 250 ml of 1 N hydrochloric acid and the mixture is stirred at 45° C. for 2 hours. It is then concentrated under reduced pressure and then diluted with 50 ml of water. The resulting solution is filtered and lyophilized to give the expected product in the form of a white solid with a yield of 95%.
M.p.=164–166° C.
$[\alpha]_D^{22}$=−28° (c=0.3; $CH_3OH$)

EXAMPLE 30

1-[[3-[(2-Methylquinolin-8-yl)oxymethyl]-2,4-dichlorophenyl]sulfonyl]-N-[2-(piperidin-4-yl)ethyl]-2-(S)-pyrrolidinecarboxamide dihydrochloride The expected product is obtained with a yield of 98% by following a procedure analogous to Example 8, starting from the compound obtained according to Preparation XXXVII.
M.p.=174° C.
$[\alpha]_D^{22}$=−30° (c=1.0; $CH_3OH$)

EXAMPLE 31

1-[[3-[(2,4-Dimethylquinolin-8-yl)oxymethyl]-2,4-dichlorophenyl]sulfonyl]-N-[(piperidin-4-yl)methyl]-2-(S)-pyrrolidinecarboxamide dihydrochloride The expected product is obtained with a yield of 97% by following a procedure analogous to Example 8, starting from the compound obtained according to Preparation XXXVIII.
M.p.=195° C.
$[\alpha]_D^{24}$=−32° (c=1.0; $CH_3OH$)

EXAMPLE 32

1-[[3-[(2,4-Dimethylquinolin-8-yl)oxymethyl]-2,4-dichlorophenyl]sulfonyl]-N-[piperidin-4-yl]-2-(S)-pyrrolidinecarboxamide dihydrochloride The expected product is obtained with a yield of 85% by following a procedure analogous to Example 8, starting from the compound obtained according to Preparation XXXIX.
M.p.=184–190° C.
$[\alpha]_D^{25}$=−14° (c=0.56; $CH_3OH$)

PREPARATION XL

1-[[3-[(2-Methylquinolin-8-yl)oxymethyl]-2,4-dichlorophenyl]sulfonyl]-N-[4-[[(1,1-dimethylethoxycarbonyl)amino]-[(1,1-dimethylethoxycarbonyl)imino]-methylamino]butyl]-2-(S)-pyrrolidinecarboxamide The expected product is obtained with a yield of 50% by following a procedure analogous to Preparation XXIII, starting from the compound obtained according to Example 29.

M.p.=82–84° C.
$[\alpha]_D^{22}$=−37° (c=0.31; CHCl$_3$)

PREPARATION XLI

1-[[3-[(2-Methylquinolin-8-yl)oxymethyl]-2,4-dichlorophenyl]sulfonyl]-N-[2-[1-[[(1,1-dimethylethoxycarbonyl)amino]-[(1,1-dimethylethoxycarbonyl)imino]methyl]piperidin-4-yl]ethyl]-2-(S)-pyrrolidinecarboxamide The expected product is obtained with a yield of 79% by following a procedure analogous to Preparation XXIII, starting from the compound obtained according to Example 30.
M.p.=80° C.
$[\alpha]_D^{22}$=−36° (c=1; CH$_3$OH)

PREPARATION XLII

1-[[3-[(2,4-Dimethylquinolin-8-yl)oxymethyl]-2,4-dichlorophenyl]sulfonyl]-N-[[1-[[(1,1-dimethylethoxycarbonyl)amino]-[(1,1-dimethylethoxycarbonyl)imino]methyl]piperidin-4-yl]methyl]-2-(S)-pyrrolidinecarboxamide The expected product is obtained with a yield of 75% by following a procedure analogous to Preparation XXIII, starting from the compound obtained according to Example 31.
M.p.=98° C.
$[\alpha]_D^{22}$=−31° (c=1.05; CH$_3$OH)

PREPARATION XLIII

1-[[3-[(2-Methylquinolin-8-yl)oxymethyl]-2,4-dichlorophenyl]sulfonyl]-2-(S)-[[4-[[(ethyl)(1,1-dimethylethoxycarbonyl)amino]-[(1,1-dimethylethoxycarbonyl)imino]methyl]piperazin-1-yl]carbonyl]pyrrolidine 8 mg (0.186.10$^{-3}$ mol) of sodium hydride as a 60% suspension in oil are added to a solution of 0.15 g (0.186.10$^{-3}$ mol) of the compound according to Preparation XXIV in 5 ml of dimethylformamide. After stirring for 5 min at room temperature, 58 mg (0.372.10$^{-3}$ mol) of ethyl iodide are added. The mixture is stirred for 20 hours at room temperature and then poured into 100 ml of water. The precipitate formed is filtered off, rinsed with water and dried in an oven under vacuum at 50° C. to give 0.14 g of the expected product in the form of a white solid (yield=90%).
M.p.=95° C.
$[\alpha]_D^{23}$=−36° (c=0.32; CH$_3$OH)

EXAMPLE 33

1-[[3-[(2-Methylquinolin-8-yl)oxymethyl]-2,4-dichlorophenyl]sulfonyl]-N-[4-[(aminoiminomethyl)amino]butyl]-2-(S)-pyrrolidinecarboxamide dihydrochloride The expected product is obtained with a yield of 70% by following a procedure analogous to Example 29, starting from the compound obtained according to Preparation XL.
M.p.=148–152° C.
$[\alpha]_D^{24}$=−31° (c=0.35; CH$_3$OH)

EXAMPLE 34

1-[[3-[(2-Methylquinolin-8-yl)oxymethyl]-2,4-dichlorophenyl]sulfonyl]-N-[2-[1-(aminoiminomethyl)piperidin-4-yl]ethyl]-2-(S)-pyrrolidinecarboxamide dihydrochloride The expected product is obtained with a yield of 82% by following a procedure analogous to Example 8, starting from the compound obtained according to Preparation XLI.

M.p.=165° C.
$[\alpha]_D^{22}$=−24.5° (c=1.05; CH$_3$OH)

EXAMPLE 35

1-[[3-[(2,4-Dimethylquinolin-8-yl)oxymethyl]-2,4-dichlorophenyl]sulfonyl]-N-[[1-(aminoiminomethyl)piperidin-4-yl]methyl]-2-(S)-pyrrolidinecarboxamide dihydrochloride The expected product is obtained with a yield of 76% by following a procedure analogous to Example 8, starting from the compound obtained according to Preparation XLII.
M.p.=211° C.
$[\alpha]_D^{22}$=−26.5° (c=1.0; CH$_3$OH)

EXAMPLE 36

1-[[3-[(2-Methylquinolin-8-yl)oxymethyl]-2,4-dichlorophenyl]sulfonyl]-2-(S)-[[4-[(ethylamino)iminomethyl]piperazin-1-yl]carbonyl]pyrrolidine bistrifluoroacetate A solution of 0.34 g (0.408.10$^{-3}$ mol) of the compound according to Preparation XLIII in 15 ml of dichloromethane is prepared, 88 mg (0.816.10$^{-3}$ mol) of anisole are then added, the mixture is cooled to 0° C. and 3 ml of trifluoroacetic acid are added. The mixture is stirred for one hour at 0° C. and then overnight at room temperature. The solvents are evaporated off under reduced pressure and the residue is taken up with isopropyl ether. The precipitate formed is filtered off, dried and then redissolved in 5 ml of water and lyophilized to give 0.23 g of the expected product in the form of a white solid (yield=65%).
M.p.=115° C.
$[\alpha]_D^{23}$=+10° (c=0.42; CH$_3$OH)

PREPARATION XLIV

1-[[3-[(2-Methylquinolin-8-yl)oxymethyl]-2,4-dichlorophenyl]sulfonyl]-N-[[1-[4-[(1,1-dimethylethoxycarbonyl)amino]-1-oxobutyl]piperidin-4-yl]methyl]-2-S)-pyrrolidinecarboxamide The expected product is obtained with a yield of 88% by following a procedure analogous to Preparation XIV, starting from the compound obtained according to Example 10 and 4-[(1,1-dimethylethoxycarbonyl)amino]butanoic acid, in the presence of N-methylmorpholine.
M.p.=98° C.
$[\alpha]_D^{22}$=−39° (c=1.05; CH$_3$OH)

PREPARATION XLV

1-[[3-[(2-Methylquinolin-8-yl)oxymethyl]-2,4-dichlorophenyl]sulfonyl]-N-[1-[2-[(1,1-dimethylethoxycarbonyl)amino]-1-oxoethyl]piperidin-4-yl]-2-(S)-pyrrolidinecarboxamide The expected product is obtained with a yield of 97% by following a procedure analogous to Preparation XLIV, starting from the compound obtained according to Example 8 and N-(1,1-dimethylethoxycarbonyl)glycine.
M.p.=94° C.
$[\alpha]_D^{22}$=−40° (c=1.03; CHCl$_3$)

PREPARATION XLVI

1-[[3-[(2-Methylquinolin-8-yl)oxymethyl]-2,4-dichlorophenyl]sulfonyl]-N-[1-[3-[(1,1-dimethylethoxycarbonyl)amino]-1-oxopropyl]piperidin-4-yl]-2-(S)-pyrrolidinecarboxamide The expected product is obtained with a yield of 97% by following a procedure analogous to Preparation XLIV, starting from the compound according to Example 8 and N-(1,1-dimethylethoxycarbonyl)-β-alanine.
M.p.=100–102° C.
$[\alpha]_D^{22}$=−39° (c=1.0; CHCl$_2$)

PREPARATION XLVII

1-[[3-[(2-Methylquinolin-8-yl)oxymethyl]-2,4-dichlorophenyl]sulfonyl]-N-[1-[4-[(1,1-dimethylethoxycarbonyl)amino]-1-oxobutyl]piperidin-4-yl]-2-(S)-pyrrolidinecarboxamide The expected product is obtained with a yield of 91% by following a procedure analogous to Preparation XLIV, starting from the compound according to Example 8 and 4-[(1,1-dimethylethoxycarbonyl)amino]butanoic acid.
M.p.=98° C.
$[\alpha]_D^{22}$=−39° (c=0.95; CHCl$_3$)

PREPARATION XLVIII

1-[[3-[(2,4-Dimethylquinolin-8-yl)oxymethyl]-2,4-dichlorophenyl]sulfonyl]-N-[1-[3-[(1,1-dimethylethoxycarbonyl)amino]-1-oxopropyl]piperidin-4-yl]-2-(S)-pyrrolidinecarboxamide The expected product is obtained with a yield of 98% by following a procedure analogous to Preparation XLVI, starting from the compound according to Example 32 and N-(1,1-dimethylethoxycarbonyl)-β-alanine.
M.p.=75–78° C.
$[\alpha]_D^{22}$=−53° (c=1.05; CH$_3$OH)

EXAMPLE 37

1-[[3-[(2-Methylquinolin-8-yl)oxymethyl]-2,4-dichlorophenyl]sulfonyl]-N-[[1-(4-amino-1-oxobutyl)piperidin-4-yl]methyl]-2-(S)-pyrrolidinecarboxamide dihydrochloride The expected product is obtained with a yield of 94% by following a procedure analogous to Example 8, starting from the compound obtained according to Preparation XLIV.
M.p.=151° C.
$[\alpha]_D^{22}$=−22.5° (c=0.95; CH$_3$OH)

EXAMPLE 38

1-[[3-[(2-Methylquinolin-8-yl)oxymethyl]-2,4-dichlorophenyl]sulfonyl]-N-[1-(2-amino-1-oxoethyl)piperidin-4-yl]-2-(S)-pyrrolidinecarboxamide dihydrochloride The expected product is obtained with a yield of 89% by following a procedure analogous to Example 8, starting from the compound obtained according to Preparation XLV.
M.p.=210° C.
$[\alpha]_D^{22}$=−8.6° (c=0.95; CH$_3$OH)

EXAMPLE 39

1-[[3-[(2-Methylquinolin-8-yl)oxymethyl]-2,4-dichlorophenyl]sulfonyl]-N-[1-(3-amino-1-oxopropyl)piperidin-4-yl]-2-(S)-pyrrolidinecarboxamide dihydrochloride The expected product is obtained with a yield of 19% by following a procedure analogous to Example 8, starting from the compound obtained according to Preparation XLVI.
M.p.=140° C.
$[\alpha]_D^{22}$=−33° (c=0.75; CHCl$_3$)

EXAMPLE 40

1-[[3-[(2-Methylquinolin-8-yl)oxymethyl]-2,4-dichlorophenyl]sulfonyl]-N-[1-(4-amino-1-oxobutyl)piperidin-4-yl]-2-(S)-pyrrolidinecarboxamide dihydrochloride The expected product is obtained with a yield of 99% by following a procedure analogous to Example 8, starting from the compound obtained according to Preparation XLVII.
M.p.=174° C.
$[\alpha]_D^{22}$=−7.7° (c=1.0; CH$_3$OH)

EXAMPLE 41

1-[[3-[(2,4-Dimethylquinolin-8-yl)oxymethyl]-2,4-dichlorophenyl]sulfonyl]-N-[1-(3-amino-1-oxopropyl)piperidin-4-yl]-2-(S)-pyrrolidinecarboxamide dihydrochloride The expected product is obtained with a yield of 98% by following a procedure analogous to Example 8, starting from the compound obtained according to Preparation XLVIII.
M.p.=89–91° C.
$[\alpha]_D^{22}$=−12.5° (c=1.1; CH$_3$OH)

PREPARATION IL

1-[[3-[(2-Methylquinolin-8-yl)oxymethyl]-2,4-dichlorophenyl]sulfonyl]-N-[[1-[4-[(1,1-dimethylethoxycarbonyl)amino]-[(1,1-dimethylethoxycarbonyl)imino]methylamino]-1-oxobutylpiperidin-4-yl]methyl]-2-(S)-pyrrolidinecarboxamide A solution of 1.9 g (2.6.10$^{-3}$ mol) of the compound obtained according to Example 37 in 40 ml of ethanol is prepared and 1.4 ml (10.10$^{-3}$ mol) of triethylamine are added, followed, after stirring for about 5 min, by 0.9 g (3.1.10$^{-3}$ mol) of N,N'-bis(1,1-dimethylethoxycarbonyl)-S-methylisothiourea {or [[[(1,1-dimethylethoxy)carbonyl]amino](methylthio)methylene]carbamic acid 1,1-dimethylethyl ester}; finally, 1.8 g (8.10$^{-3}$ mol) of mercuric oxide are added and the reaction medium is stirred at room temperature for 18 hours. It is filtered and the filtrate is then concentrated under reduced pressure. The residue is purified by chromatography on silica gel using ethyl acetate as the eluent to give 1.7 g of the expected product in the form of white crystals (yield=69%).
M.p.=90° C.
$[\alpha]_D^{20}$=−32° (c=1.05; CH$_3$OH)

PREPARATION L

1-[[3-[(2-Methylquinolin-8-yl)oxymethyl]-2,4-dichlorophenyl]sulfonyl]-N-[1-[2-[[(1,1-dimethylethoxycarbonyl)amino]-[(1,1-dimethylethoxycarbonyl)imino]methylamino]-1-oxoethyl]piperidin-4-yl]-2-(S)-pyrrolidinecarboxamide The expected product is obtained with a yield of 15% by following a procedure analogous to Preparation IL, starting from the compound obtained according to Example 38.
M.p.=123° C.
$[\alpha]_D^{22}$=−32.5° (c=0.9; CHCl$_3$)

PREPARATION LI

1-[[3-[(2-Methylquinolin-8-yl)oxymethyl]-2,4-dichlorophenyl]sulfonyl]-N-[1-[3-[[(1,1-dimethylethoxycarbonyl)amino]-[(1,1-dimethylethoxycarbonyl)imino]methylamino]-1-oxopropyl]piperidin-4-yl]-2-(S)-pyrrolidinecarboxamide The expected product is obtained with a yield of 77% by following a procedure analogous to Preparation IL, starting from the compound obtained according to Example 39.

M.p.=112° C.
$[\alpha]_D^{22}$=−23° (c=1.3; CH$_3$OH)

PREPARATION LII

1-[[3-[(2-Methylquinolin-8-yl)oxymethyl]-2,4-dichlorophenyl]sulfonyl]-N-[1-[4-[[(1,1-dimethylethoxycarbonyl)amino]-[(1,1-dimethylethoxycarbonyl)imino]methylamino]-1-oxobutyl]piperidin-4-yl]-2-(S)-pyrrolidinecarboxamide The expected product is obtained with a yield of 74% by following a procedure analogous to Preparation IL, starting from the compound obtained according to Example 40.
M.p.=102–105° C.
$[\alpha]_D^{20}$=−24° (c=1.05; CH$_3$OH)

PREPARATION LIII

1-[[3-[(2,4-Dimethylquinolin-8-yl)oxymethyl]-2,4-dichlorophenyl]sulfonyl]-N-[1-[3-[[(1,1-dimethylethoxycarbonyl)amino]-[(1,1-dimethylethoxycarbonyl)imino]methylamino]-1-oxopropyl]piperidin-4-yl]-2-(S)-pyrrolidinecarboxamide The expected product is obtained with a yield of 86% by following a procedure analogous to Preparation IL, starting from the compound obtained according to Example 41.
M.p.=115–117° C.
$[\alpha]_D^{22}$=−22° (c=0.92; CH$_3$OH)

EXAMPLE 42

1-[[3-[(2-Methylquinolin-8-yl)oxymethyl]-2,4-dichlorophenyl]sulfonyl]-N-[[1-[4-[(aminoiminomethyl)amino]-1-oxobutyl]piperidin-4-yl]methyl]-2-(S)-pyrrolidinecarboxamide dihydrochloride The expected product is obtained with a yield of 75% by following a procedure analogous to Example 8, starting from the compound obtained according to Preparation IL.
M.p.=178° C.
$[\alpha]_D^{22}$=−19° (c=1.05; CH$_3$OH)

EXAMPLE 43

1-[[3-[(2-Methylquinolin-8-yl)oxymethyl]-2,4-dichlorophenyl]sulfonyl]-N-[1-[2-[(aminoiminomethyl)amino]-1-oxoethyl]piperidin-4-yl]-2-(S)-pyrrolidinecarboxamide dihydrochloride The expected product is obtained with a yield of 83% by following a procedure analogous to Example 8, starting from the compound obtained according to Preparation L.
M.p.=194° C.
$[\alpha]_D^{22}$=−8.7° (c=0.65; CH$_3$OH)

EXAMPLE 44

1-[[3-[(2-Methylquinolin-8-yl)oxymethyl]-2,4-dichlorophenyl]sulfonyl]-N-[1-[3-[(aminoiminomethyl)amino]-1-oxopropyl]piperidin-4-yl]-2-(S)-pyrrolidinecarboxamide dihydrochloride The expected product is obtained with a yield of 81% by following a procedure analogous to Example 8, starting from the compound obtained according to Preparation LI.
M.p.=170° C.
$[\alpha]_D^{22}$=−11.5° (c=1.1; CH$_3$OH)

EXAMPLE 45

1-[[3-[(2-Methylquinolin-8-yl)oxymethyl]-2,4-dichlorophenyl]sulfonyl]-N-[1-[4-[(aminoiminomethyl)amino]-1-oxobutyl]piperidin-4-yl]-2-(S)-pyrrolidinecarboxamide dihydrochloride The expected product is obtained with a yield of 85% by following a procedure analogous to Example 8, starting from the compound obtained according to Preparation LII.
M.p.=190° C.
$[\alpha]_D^{22}$=−6.1° (c=1.05; CH$_3$OH)

EXAMPLE 46

1-[[3-[(2,4-Dimethylquinolin-8-yl)oxymethyl]-2,4-dichlorophenyl]sulfonyl]-N-[1-[3-[(aminoiminomethyl)amino]-1-oxopropyl]piperidin-4-yl]-2-(S)-pyrrolidinecarboxamide dihydrochloride The expected product is obtained with a yield of 74% by following a procedure analogous to Example 8, starting from the compound obtained according to Preparation LIII.
M.p.=174° C.
$[\alpha]_D^{22}$=−9.6° (c=1.0; CH$_3$OH)

The activity of the products according to the invention was evaluated in respect of their ability to bind to the bradykinin receptors. Kinins, of which bradykinin is the main representative, actually form a group of small peptides which make an important contribution to the inflammatory response and therefore appear to be involved in the pathophysiology of inflammatory diseases. Furthermore, bradykinin is one of the most potent analgesics known. Kinins activate two types of receptor, called $B_1$ and $B_2$, which belong to the large family of receptors with seven transmembrane domains coupled to the G proteins. In the present invention we describe compounds which bind to the $B_2$ receptor and thereby block the binding of bradykinin to this receptor.

The following pharmacological test is used: Ileum segments are isolated from male guinea-pigs of the Dunkin-Hartley strain (Iffa Credo, l'Arbresle, France) and ground in the following TES buffer: TES 25 mM, 1,10-phenanthroline 1 mM (pH 6.8), bacitracin 140 µg/ml, BSA 1 g/l. The membranes are then isolated by centrifugation (18,000 rpm; 20 min; 4° C.). The binding studies are carried out in the TES buffer using [$^3$H]-bradykinin (120 pM) and 50 µg of membrane protein per test (final volume 500 µl) with an equilibrium time of 90 min at 20° C. The percentage inhibition of the binding of [$^3$H]-bradykinin is then determined in the presence of one of the test compounds according to the invention at a concentration of 10$^{-6}$ M.

The results obtained from these tests (shown as "activity") are collated in Table I below with reference to the Examples given in the description.

The compounds of the present invention which inhibit the binding of [$^3$H]-bradykinin to the guinea-pig $B_2$ receptor (see Table I) also bind to the human $B_2$ receptor cloned and transfected in a stable manner into CHO cells (Chinese Hamster Ovary cells). Thus, in this test, some compounds inhibit the binding of [$^3$]-bradykinin to the $B_2$ receptor by at least 95% at a concentration of 10 µM.

The compounds of the present invention are useful in the treatment of pain and particularly in the treatment of numerous pathological conditions involving bradykinin or its homologs. These pathological conditions include septic and hemorrhagic shock, anaphylactic reactions, arthrosis, rheumatoid polyarthritis, rhinitis, asthma, inflammatory diseases of the gastrointestinal tract (for example colitis, rectitis, Crohn's disease), pancreatitis, certain carcinomas, hereditary angioedema, migraine, encephalomyelitis, meningitis, cerebrovascular complications (especially those caused by cerebral traumatic shock), certain neurological disorders, vascular inflammatory states (for example atherosclerosis and arteritis of the lower limbs), painful states (for example headache, toothache, menstrual pain), premature uterine contractions, cystitis and burns. The compounds according to the invention can also be useful for the potentiation of antiviral agents.

The compounds of the present invention, which can be used in the form of the free base or in the form of their non-toxic addition salts in association with a physiologically acceptable excipient, will generally be prescribed in therapeutics at doses of about 1 to 1000 mg/day in a form which can be administered orally, by intravenous, intramuscular or subcutaneous injection, transdermally, by means of aerosols or by means of suppositories.

The compounds may also be administered topically, for example in the form of gels or ointments.

The compounds of the present invention are also useful as pharmacological reagents, especially for the study of hormone-receptor interactions. Use as a pharmacological reagent may require a radiolabeled derivative of one of the compounds according to the invention (for example with tritium [$^3$H] or sulfur [$^{35}$S]) in order to obtain a radioligand intended for conformational studies of the bradykinin $B_2$ receptor or for binding tests involving this type of receptor, for example for the evaluation of novel compounds which are capable of exhibiting an affinity for the bradykinin $B_2$ receptor.

According to the invention, a therapeutic composition is recommended which is characterized in that it contains, in association with a physiologically acceptable excipient, at least one active ingredient selected from the group consisting of the compounds of formula I and their non-toxic addition salts.

TABLE I

| Ex. | $R_1$ | $R_2$ | $R_3$ | SALT* | ACTIVITY % |
|---|---|---|---|---|---|
| 1 | H | H | piperazine with two CH$_3$ groups (NH) | — | / |
| 2 | H | H | piperazine-NH | — | 100 |
| 3 | H | H | —NH—(CH$_2$)$_2$—NH$_2$ | — | 100 |
| 4 | CH$_3$ | H | —NH—(CH$_2$)$_2$—NH$_2$ | — | |
| 5 | CH$_3$ | H | piperazine-NH | tac | 100 |
| 6 | H | H | —N(CH$_3$)—(CH$_2$)$_2$—NH$_2$ | tac | / |
| 7 | CH$_3$ | OH | piperazine-NH | tac | / |

TABLE I-continued

[Structure: 4-R1-2-methylquinoline-8-yl-O-CH2- linked to 2,6-dichlorophenyl-SO2-N(pyrrolidine with R2 and C(=O)R3)]

| Ex. | R₁ | R₂ | R₃ | SALT* | ACTIVITY % |
|---|---|---|---|---|---|
| 8 | H | H | —NH—(4-piperidinyl)-H | Chl | 100 |
| 9 | H | H | —NH—(CH₂)₃—NH₂ | Chl | 100 |
| 10 | H | H | —NH—CH₂—(4-piperidinyl)-H | Chl | 100 |
| 11 | H | H | —O—(4-piperidinyl)-H | Chl | / |
| 12 | H | H | —O—CH₂—(4-piperidinyl)-H | Chl | / |
| 13 | CH₃ | H | —NH—(CH₂)₃—NH₂ | Chl | / |
| 14 | CH₃ | H | —N(piperazinyl)-C(=NH)NH₂ | tac | 98 |
| 15 | CH₃ | OH | —N(piperazinyl)-C(=NH)NH₂ | tac | 100 |
| 16 | H | H | —NH—(CH₂)₂—HN—C(=NH)NH₂ | tac | 100 |
| 17 | H | H | —N(CH₃)—(CH₂)₂—HN—C(=NH)NH₂ | tac | / |
| 18 | H | H | —O—CH₂—(4-piperidinyl)-N-C(=NH)NH₂ | tac | / |

TABLE I-continued

[Structure: 4-R₁-2-methylquinolin-8-yl-O-CH₂ linked to 2,6-dichlorophenyl bearing SO₂-N(pyrrolidine) where pyrrolidine has R₂ at 4-position and C(=O)R₃ at 2-position]

| Ex. | R₁ | R₂ | R₃ | SALT* | ACTIVITY % |
|---|---|---|---|---|---|
| 19 | CH₃ | H | —NH—(CH₂)₂—HN—C(=NH)NH₂ | Chl | 97 |
| 20 | CH₃ | H | —NH—(CH₂)₃—HN—C(=NH)NH₂ | Chl | 98 |
| 21 | H | H | —NH—(CH₂)₃—HN—C(=NH)NH₂ | Chl | / |
| 22 | H | H | —NH—CH₂—(4-piperidyl)-N—C(=NH)NH₂ | Chl | 98 |
| 23 | H | H | —NH—(4-piperidyl)-N—C(=NH)NH₂ | Chl | 100 |
| 24 | H | H | (4-methylpiperazin-1-yl)—C(=NH)NH₂ | Chl | 98 |
| 25 | H | H | (2,6-dimethyl-4-methylpiperazin-1-yl)—C(=NH)NH₂ | Chl | 100 |
| 26 | H | H | —O—(4-piperidyl)-N—C(=NH)NH₂ | Chl | / |

TABLE I-continued

| Ex. | R₁ | R₂ | R₃ | SALT* | ACTIVITY % |
|---|---|---|---|---|---|
| 27 | H | H | N-methylpiperazine-C(=N-CH(CH₃)₂)-NH-CH(CH₃)₂ | Chl | 100 |
| 28 | H | H | N-methylpiperazine-C(=N-cyclohexyl)-NH-cyclohexyl | Chl | / |
| 29 | H | H | —NH—(CH₂)₄—NH₂⁻ | Chl | |
| 30 | H | H | —NH—(CH₂)₂—(piperidin-4-yl)N—H | Chl | |
| 31 | CH₃ | H | —NH—CH₂—(piperidin-4-yl)N—H | Chl | |
| 32 | CH₃ | H | —NH—(piperidin-4-yl)N—H | Chl | |
| 33 | H | H | —NH—(CH₂)₄—NH—C(=NH)NH₂ | Chl | |
| 34 | H | H | —NH—(CH₂)₂—(piperidin-4-yl)N—C(=NH)NH₂ | Chl | |
| 35 | CH₃ | H | —NH—CH₂—(piperidin-4-yl)N—C(=NH)NH₂ | Chl | |

TABLE I-continued
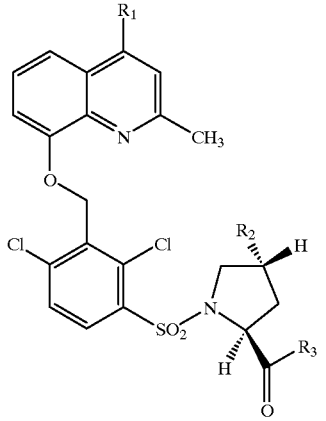
| Ex. | R₁ | R₂ | R₃ | SALT* | ACTIVITY % |
|---|---|---|---|---|---|
| 36 | H | H | 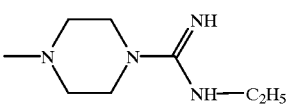 | tac | |
| 37 | H | H | 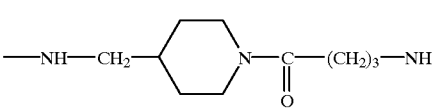 | Chl | |
| 38 | H | H | 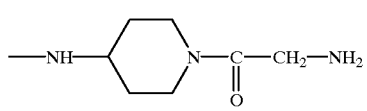 | Chl | |
| 39 | H | H | 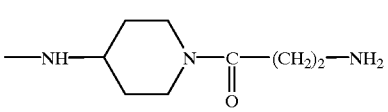 | Chl | |
| 40 | H | H | 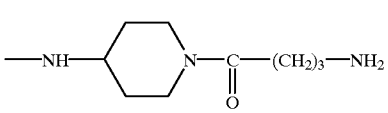 | Chl | |
| 41 | CH₃ | H | 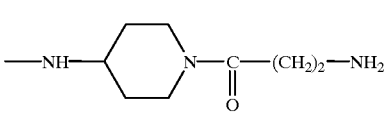 | Chl | |
| 42 | H | H | 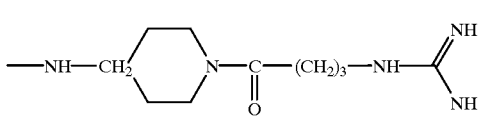 | Chl | |
| 43 | H | H | 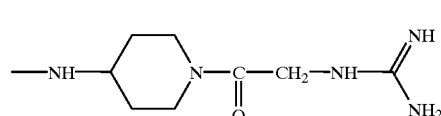 | Chl | |
| 44 | H | H | 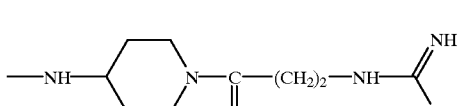 | Chl | |

TABLE I-continued

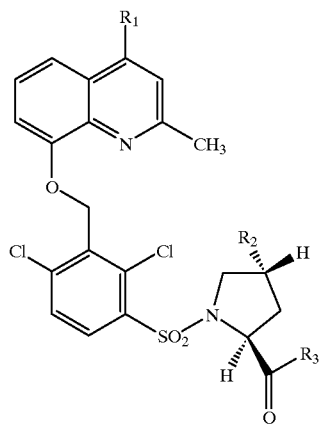

| Ex. | $R_1$ | $R_2$ | $R_3$ | SALT* | ACTIVITY % |
|---|---|---|---|---|---|
| 45 | H | H | 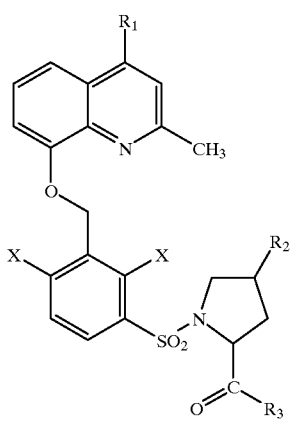 | Chl | |
| 46 | $CH_3$ | H | 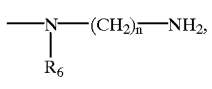 | Chl | |

Note:
*: nature of the salt: "tac" denotes the trifluoroacetic acid salt and "Chl" denotes the hydrochloric acid salt.

What is claimed is:

1. An N-Benzenesulfonylpyrrolidine compound, which is selected from the group consisting of
   (i) compounds of the formula $$(I)$$

[structural formula of compound I]

in which:
X is a halogen atom,
$R_1$ is a hydrogen atom or a $C_1$–$C_3$ alkyl group having a linear or branched hydrocarbon chain,
$R_2$ is a hydrogen atom or an OH group, and
$R_3$ is a group

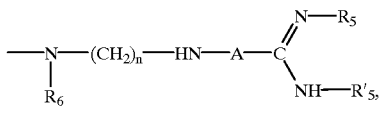

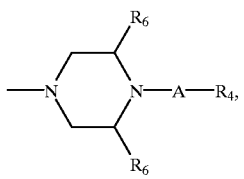

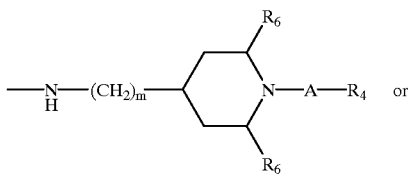

or

-continued

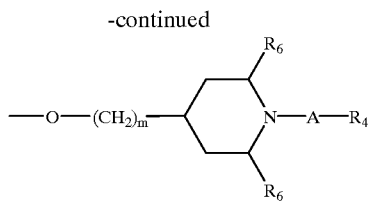

in which:

A is a single bond or a group —CO—(CH$_2$)$_p$—NH—,

R$_4$ is a hydrogen atom or a group

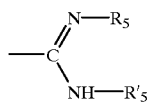

R$_5$ and R'$_5$, which are identical or different, are each a hydrogen atom or a linear, branched or cyclized C$_1$–C$_6$ alkyl group, R$_6$ is a hydrogen atom or a linear or branched C$_1$–C$_3$ alkyl group, m is an integer having a value of 0, 1 or 2, n is an integer having a value of 2, 3 or 4, and p is an integer having a value of 1, 2 or 3; and (ii) their addition salts.

2. A compound according to claim 1, wherein X is a chlorine atom.

3. An intermediate compound useful for the preparation of the compounds of formula I which is represented by the formula

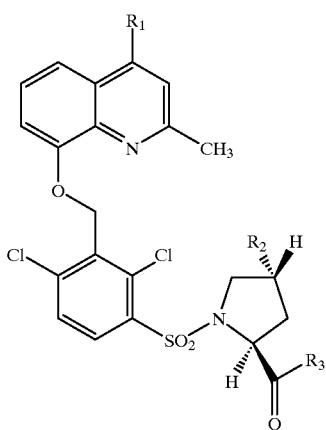

in which:

R$_1$ is CH$_3$,

R$_2$ is H or OH, and

R$_3$ is OH or OCH$_3$.

4. A method of treating pathological conditions involving bradykinin, comprising administering to a patient in need of such a treatment a therapeutically effective amount of a compound selected from the group consisting of the compounds of the formula I and non-toxic acid addition salts thereof as claimed in claim 1.

5. A method according to claim 4 for the treatment of painful or inflammatory disorders comprising administering to a patient in need of such a treatment a therapeutically effective amount of a compound selected from the group consisting of the compounds of the formula I and non-toxic acid addition salts thereof as claimed in claim 1.

6. A pharmaceutical composition comprising a physiologically acceptable excipient and at least one active ingredient selected from the group consisting of the compounds of formula I and non-toxic addition salts thereof as claimed in claim 1.

7. A method for preparing a compound of the formula I as claimed in claim 1, wherein R$_3$ is a group

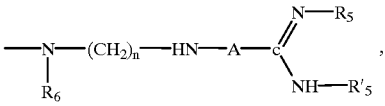

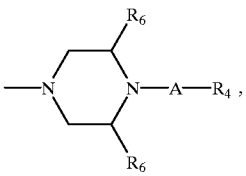

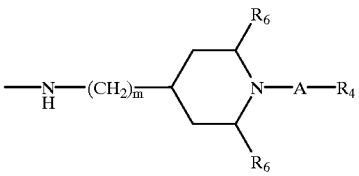

or

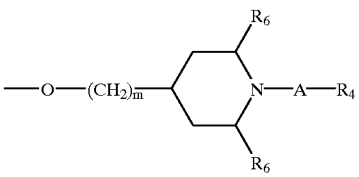

A is a single bond or a group —CO—(CH$_2$)$_p$—NH—,

R$_4$ is a group

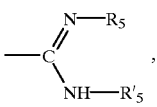

R$_5$ and R'$_5$ are each a hydrogen atom,

R$_6$ is a hydrogen atom or a linear or branched C$_1$–C$_3$ alkyl group, m is an integer having a value of 0, 1 or 2, n is an integer having a value of 2, 3 or 4, and p is an integer having a value of 1, 2 or 3, said method comprising:

1) reacting a compound of the formula

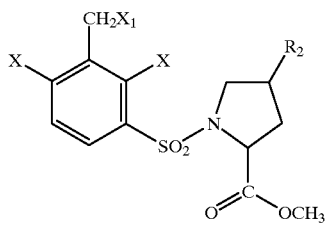

(II)

in which X and $X_1$ are each a halogen atom, $R_2$ is a hydrogen atom or an OH group, and the carbon atom carrying the group $COOCH_3$ and the carbon atom carrying a group $R_2$ different from H are independently of the (R,S), (R) or (S) configuration, with a compound of the formula

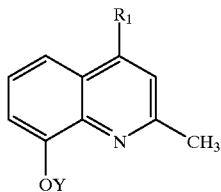

(III)

in which:

$R_1$ is a hydrogen atom or a $C_1$–$C_3$ alkyl group, and

Y is an alkali metal, in an anhydrous solvent, at a temperature of between 0 and 50° C., for 0.5 to 5 hours, to give a compound of the formula

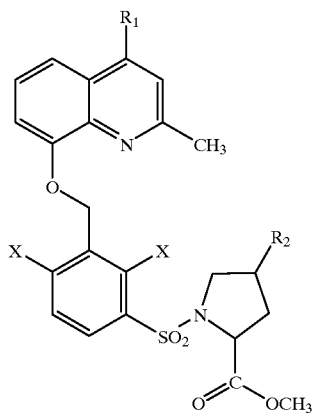

(IV)

in which X, $R_1$ and $R_2$ are as defined above and the carbon atoms carrying the substituents $COOCH_3$ and $R_2$ each retain the same configuration as in the above compound of the formula II;

2) subjecting the resulting compound of the formula IV to an alkaline hydrolysis reaction with an aqueous solution of a metal hydroxide in an inert solvent, at a temperature of between 10 and 50° C., for 1 to 30 hours, to give the acid compound of the formula

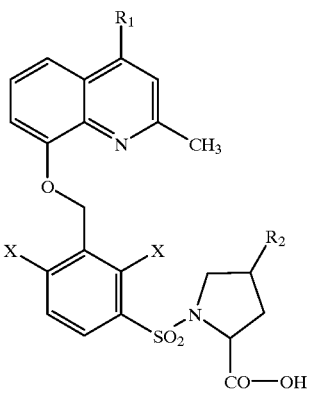

(V)

in which X, $R_1$ and $R_2$ are as defined above;

3) reacting the resulting acid of the formula V with an alcohol or an amine compound of the formula

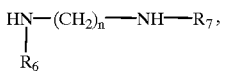

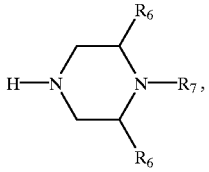

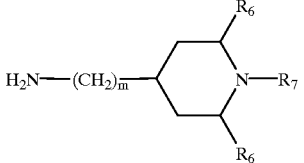

or

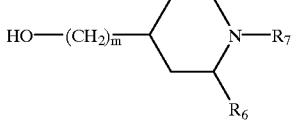

in which:

m is 0, 1 or 2, n is 2, 3 or 4, $R_6$ is a hydrogen atom or a $C_1$–$C_3$ alkyl group, and $R_7$ is an amino-protecting group or a hydrogen atom, in a solvent, in the presence of at least one activator, at a temperature close to room temperature, for 2 to 50 hours, to give a compound of the formula

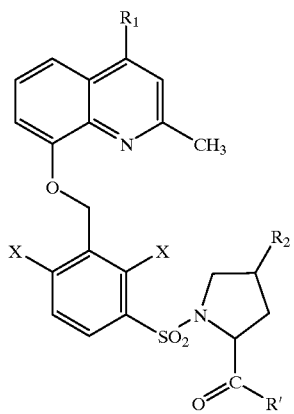

(VI)

in which:
X, R₁ and R₂ are as defined above and R' is a group:

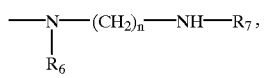

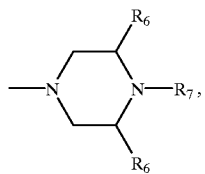

or

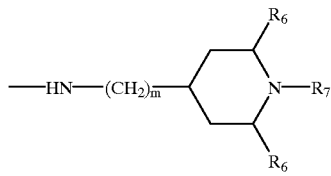

or

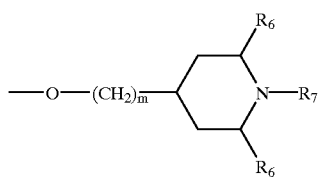

in which m, n, R₆ and R₇ are as defined above; and 4) optionally, when R₇ is an amino-protecting group, deprotecting the compound of the formula VI thus obtained with an acid, to give a compound of the formula VI in which R₇ is a hydrogen atom and which corresponds to the compound of formula I in which A is a single bond and R₄ is a hydrogen atom), 5) reacting the compound of formula VI obtained according to step 3) or 4) and in which R₇ is H with a compound of the formula

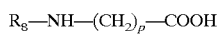

in which p is a number equal to 1, 2 or 3, and

R₈ is an amino-protecting group, in a solvent, in the presence of at least one activator, at a temperature close to room temperature, for 2 to 50 hours, to give a compound of the formula

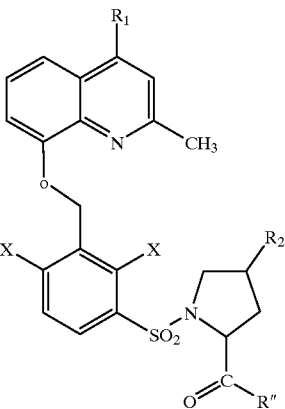

(VII)

in which X, R₁ and R₂ are as defined above and R" is a group

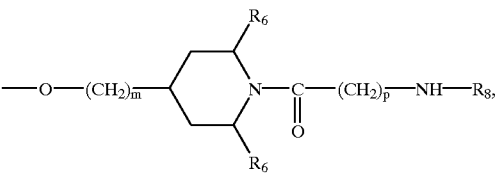

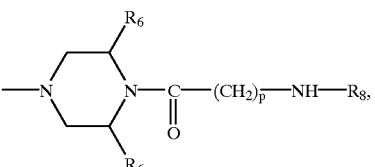

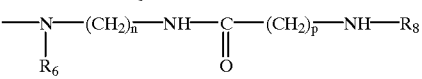

or

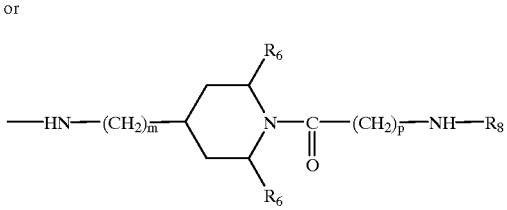

in which m, n, p, R₆ and R₈ are as defined above;

6) reacting the compound of the formula VII thus obtained with an acid for replacing the amino-protecting group R₈ with a hydrogen atom in order to give a compound of the formula

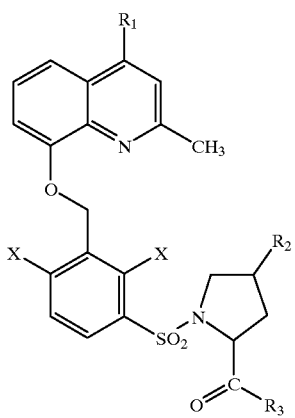

(I)

in which X, $R_1$ and $R_2$ are as defined above and $R_3$ is a group

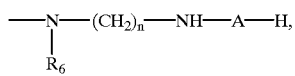

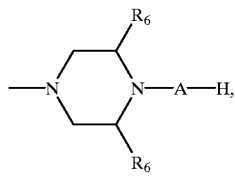

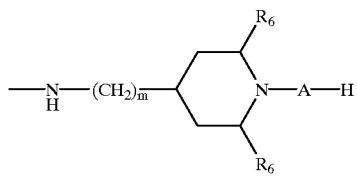

or

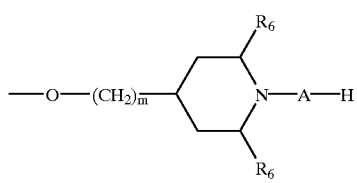

in which m, n and $R_6$ are as defined above and A is the group —CO—$(CH_2)_p$—NH—, in which p is a number equal to 1, 2 or 3, 7) reacting a compound of the formula VI obtained according to step 3) or 4) above, in which A is a single bond and $R_7$ is H, or a compound of the formula I obtained according to step 6) above in which A is a group —CO—$(CH_2)_p$—NH—, with a compound of the formula

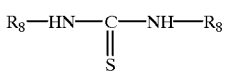

in which $R_8$ is an amino-protecting group of the oxycarbonyl type, in a solvent, in the presence of a base and in the presence of mercuric chloride, at a temperature of between 0 and 30° C., for 1 to 6 hours, to give the compound of the formula (VII)

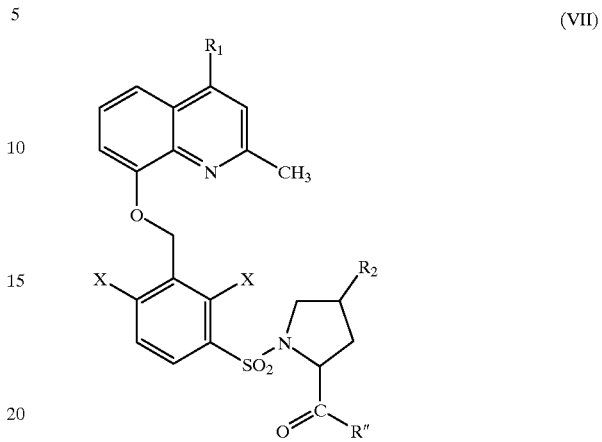

in which $R_1$, $R_2$ and X are as defined above and R″ is a group

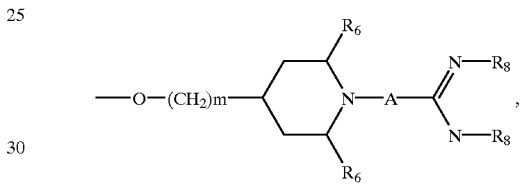

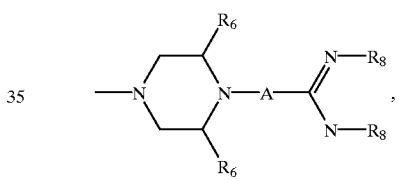

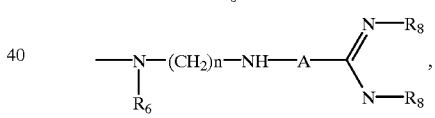

or

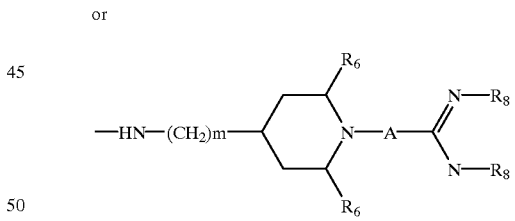

in which:

A is a single bond or the group —CO—$(CH_2)_p$, —NH—, and n, m, p, $R_6$ and $R_8$ are as defined above; and 8) deprotecting the compound of formula VII thus obtained for replacing the amino-protecting group $R_8$ with a hydrogen atom in order to give a compound of the formula I in which $R_4$ is a group —C(=$NR_5$)NHR′$_5$ and $R_5$ and R′$_5$ are each a hydrogen atom.

* * * * *